US009265577B2

(12) United States Patent
Raghavan et al.

(10) Patent No.: US 9,265,577 B2
(45) Date of Patent: Feb. 23, 2016

(54) METHODS AND SYSTEMS FOR PROVIDING PLANNING AND DISPENSATION OF RESEARCH AND/OR TREATMENT FOR BRAIN DISEASE

(75) Inventors: Raghu Raghavan, Baltimore, MD (US); Stuart A. Grossman, Towson, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1850 days.

(21) Appl. No.: 12/116,765

(22) Filed: May 7, 2008

(65) Prior Publication Data

US 2009/0024181 A1    Jan. 22, 2009

Related U.S. Application Data

(60) Provisional application No. 60/938,863, filed on May 18, 2007.

(51) Int. Cl.
*A61B 19/00* (2006.01)
*G06T 7/00* (2006.01)
*G06F 19/00* (2011.01)

(52) U.S. Cl.
CPC .............. *A61B 19/00* (2013.01); *G06T 7/0012* (2013.01); *A61B 19/50* (2013.01); *A61B 2019/501* (2013.01); *A61B 2019/562* (2013.01); *G06F 19/3437* (2013.01); *G06T 2207/30016* (2013.01)

(58) Field of Classification Search
CPC .. A61B 19/00; A61B 19/50; A61B 2019/501; A61B 2019/562; G06F 19/3437; G06T 2207/30016; G06T 7/0012
USPC .......... 600/407, 410, 416, 419–420; 382/128
See application file for complete search history.

(56) References Cited

U.S. PATENT DOCUMENTS 4,014,319 A    3/1977  Favre
4,026,276 A    5/1977  Chubbuck
(Continued)

FOREIGN PATENT DOCUMENTS

EP    0 702 966    3/1996
EP    0 709 115    5/1996
(Continued)

OTHER PUBLICATIONS

Zhao et al., "Effect of heterogeneous vasculature on interstitial transport within a solid tumor", Microvascular Research, pp. 224-236. Available online Dec. 24, 2006.*
(Continued)

*Primary Examiner* — Katherine Fernandez
(74) *Attorney, Agent, or Firm* — DLA Piper LLP (US)

(57) ABSTRACT

Methods and systems for providing planning and dispensation of research and/or treatment for brain disease. Radiological information is generated in a region of interest in an area of the a brain of an individual using a radiological imaging system. A physiological states model is constructed which assesses physiological states of the region of interest. Locations of sources of interstitial fluid flow, fluid conductivities of paths, and anatomical information in the region of interest are obtained using the radiological imaging information. Velocities of the interstitial fluid flow in the region of interest are computed using the physiological states model, the locations of sources of interstitial flow, the fluid conductivities, and the anatomic information. A model of the area of the brain is created, the model including the region of interest.

76 Claims, 20 Drawing Sheets

(56) References Cited

U.S. PATENT DOCUMENTS

| | | |
|---|---|---|
| 4,062,354 A | 12/1977 | Taylor et al. |
| 4,080,653 A | 3/1978 | Barnes, Jr. et al. |
| 4,114,603 A | 9/1978 | Wilkinson |
| 4,114,606 A | 9/1978 | Seylar |
| 4,147,161 A | 4/1979 | Ikebe et al. |
| 4,156,422 A | 5/1979 | Hildebrandt et al. |
| 4,173,228 A | 11/1979 | Van Steenwyk et al. |
| 4,210,029 A | 7/1980 | Porter |
| 4,265,252 A | 5/1981 | Chubbuck et al. |
| 4,340,038 A | 7/1982 | McKean |
| 4,354,506 A | 10/1982 | Sakaguchi et al. |
| 4,385,636 A | 5/1983 | Cosman |
| 4,438,773 A | 3/1984 | Letterio |
| 4,465,075 A | 8/1984 | Swartz |
| 4,471,786 A | 9/1984 | Inagaki et al. |
| 4,549,556 A | 10/1985 | Tarjan et al. |
| 4,600,013 A | 7/1986 | Landy et al. |
| 4,621,647 A | 11/1986 | Loveland |
| 4,627,443 A | 12/1986 | Chubbuck et al. |
| 4,677,985 A | 7/1987 | Bro et al. |
| 4,703,757 A | 11/1987 | Cohen |
| 4,711,246 A | 12/1987 | Alderson |
| 4,723,556 A | 2/1988 | Sussman |
| 4,738,267 A | 4/1988 | Lazorthes et al. |
| 4,772,257 A | 9/1988 | Hakim et al. |
| 4,800,898 A | 1/1989 | Hess et al. |
| 4,805,634 A | 2/1989 | Ullrich et al. |
| 4,841,986 A | 6/1989 | Marchbanks |
| 4,858,619 A | 8/1989 | Toth |
| 4,883,666 A | 11/1989 | Sabel et al. |
| 4,892,538 A | 1/1990 | Aebischer et al. |
| 4,903,707 A | 2/1990 | Knute et al. |
| 4,995,401 A | 2/1991 | Bunegin et al. |
| 5,000,049 A | 3/1991 | Cooper et al. |
| 5,003,497 A | 3/1991 | Priem |
| 5,005,584 A | 4/1991 | Little |
| 5,006,122 A | 4/1991 | Wyatt et al. |
| 5,042,486 A | 8/1991 | Pfeiler et al. |
| 5,074,310 A | 12/1991 | Mick |
| 5,104,403 A | 4/1992 | Brotzu et al. |
| 5,107,847 A | 4/1992 | Knute et al. |
| 5,108,364 A | 4/1992 | Takezawa et al. |
| 5,113,868 A | 5/1992 | Wise et al. |
| 5,117,835 A | 6/1992 | Mick |
| 5,125,888 A | 6/1992 | Howard et al. |
| 5,160,325 A | 11/1992 | Nichols et al. |
| 5,171,217 A | 12/1992 | March et al. |
| 5,190,744 A | 3/1993 | Rocklage et al. |
| 5,191,898 A | 3/1993 | Millar |
| 5,201,723 A | 4/1993 | Quinn |
| 5,205,289 A | 4/1993 | Hardy et al. |
| 5,211,165 A | 5/1993 | Dumoulin et al. |
| 5,230,338 A | 7/1993 | Allen et al. |
| 5,255,680 A | 10/1993 | Darrow et al. |
| 5,291,899 A | 3/1994 | Watanabe et al. |
| 5,307,808 A | 5/1994 | Dumoulin et al. |
| 5,318,025 A | 6/1994 | Dumoulin et al. |
| 5,325,865 A | 7/1994 | Beckman et al. |
| 5,344,439 A | 9/1994 | Otten |
| 5,383,454 A | 1/1995 | Bucholz |
| 5,405,316 A | 4/1995 | Magram |
| 5,487,739 A | 1/1996 | Aebischer et al. |
| 5,494,655 A | 2/1996 | Rocklage et al. |
| 5,531,673 A | 7/1996 | Helenowski |
| 5,583,902 A | 12/1996 | Bae |
| 5,607,418 A | 3/1997 | Arzbaecher |
| 5,707,335 A | 1/1998 | Howard et al. |
| 5,720,720 A | 2/1998 | Laske et al. |
| 5,733,322 A | 3/1998 | Starkebaum |
| 5,735,814 A | 4/1998 | Elsberry et al. |
| 5,738,666 A | 4/1998 | Watson et al. |
| 5,772,625 A | 6/1998 | Krueger et al. |
| 5,779,694 A | 7/1998 | Howard et al. |
| 5,820,589 A | 10/1998 | Torgerson et al. |
| 5,821,011 A | 10/1998 | Taylor et al. |
| 5,826,576 A | 10/1998 | West |
| 5,833,947 A | 11/1998 | Rocklage et al. |
| 5,836,935 A | 11/1998 | Ashton et al. |
| 5,843,093 A | 12/1998 | Howard, III |
| 5,843,148 A | 12/1998 | Gijsbers et al. |
| 5,843,150 A | 12/1998 | Dreessen et al. |
| 5,858,009 A | 1/1999 | Jonkman |
| 5,861,019 A | 1/1999 | Sun et al. |
| 5,919,135 A | 7/1999 | Lemelson |
| 5,964,705 A | 10/1999 | Truwit et al. |
| 6,026,316 A | 2/2000 | Kucharczyk et al. |
| 6,061,587 A | 5/2000 | Kucharczyk et al. |
| 6,119,065 A | 9/2000 | Shimada et al. |
| 6,210,967 B1 | 4/2001 | Bard |
| 6,272,370 B1 | 8/2001 | Gillies et al. |
| 6,293,282 B1 | 9/2001 | Lemelson |
| 6,298,259 B1 | 10/2001 | Kucharczyk et al. |
| 6,316,181 B1 | 11/2001 | Fillmore et al. |
| 6,319,682 B1 | 11/2001 | Hochman |
| 6,321,105 B1 | 11/2001 | Jenkins et al. |
| 6,381,562 B2 | 4/2002 | Keane |
| 6,430,430 B1 * | 8/2002 | Gosche ............ 600/410 |
| 6,446,055 B1 | 9/2002 | Grand |
| 6,464,662 B1 | 10/2002 | Raghavan et al. |
| 6,468,506 B1 | 10/2002 | Rossling et al. |
| 6,470,220 B1 | 10/2002 | Kraus, Jr. et al. |
| 6,491,894 B1 | 12/2002 | Ruoslahti et al. |
| 6,497,872 B1 | 12/2002 | Weiss et al. |
| 6,498,942 B1 | 12/2002 | Esenaliev et al. |
| 6,503,478 B2 | 1/2003 | Chaiken et al. |
| 6,507,747 B1 | 1/2003 | Gowda et al. |
| 6,514,519 B1 | 2/2003 | Nagler |
| 6,521,210 B2 | 2/2003 | Ohkawa |
| 6,549,803 B1 * | 4/2003 | Raghavan et al. ............ 600/431 |
| 6,560,475 B1 | 5/2003 | Viswanathan |
| 6,567,684 B1 | 5/2003 | Chenevert et al. |
| 6,572,579 B1 | 6/2003 | Viswanathan et al. |
| 6,587,706 B1 | 7/2003 | Viswanathan |
| 6,669,935 B1 | 12/2003 | Oldfield et al. |
| 6,697,661 B2 | 2/2004 | Raghavan et al. |
| 6,749,833 B2 | 6/2004 | Raghavan et al. |
| 6,836,569 B2 | 12/2004 | Le Pennec et al. |
| 7,048,716 B1 | 5/2006 | Kucharczyk et al. |
| 7,182,933 B2 | 2/2007 | Goetz et al. |
| 7,195,761 B2 | 3/2007 | Holtzman et al. |
| 7,231,075 B2 | 6/2007 | Raghavan et al. |
| 7,266,227 B2 | 9/2007 | Pedain et al. |
| 7,305,331 B2 | 12/2007 | Allen et al. |
| 2002/0010384 A1 | 1/2002 | Shahidi et al. |
| 2002/0114780 A1 | 8/2002 | Bankiewicz et al. |
| 2002/0168618 A1 | 11/2002 | Anderson et al. |
| 2003/0028090 A1 | 2/2003 | Raghavan et al. |
| 2004/0006259 A1 | 1/2004 | Pedain et al. |
| 2004/0043418 A1 | 3/2004 | Holtzman et al. |
| 2004/0138551 A1 | 7/2004 | Hartlep et al. |
| 2004/0215143 A1 | 10/2004 | Brady et al. |
| 2004/0236554 A1 | 11/2004 | Raghavan et al. |
| 2005/0031210 A1 * | 2/2005 | Shen et al. ............ 382/215 |
| 2005/0101855 A1 | 5/2005 | Miga et al. |
| 2005/0186544 A1 * | 8/2005 | Raghavan et al. ............ 434/262 |
| 2005/0207631 A1 * | 9/2005 | Martens et al. ............ 382/131 |
| 2005/0265589 A1 | 12/2005 | Raghavan et al. |
| 2005/0267360 A1 | 12/2005 | Birkenbach et al. |
| 2006/0122492 A1 * | 6/2006 | Kucharczyk et al. ......... 600/420 |
| 2006/0129324 A1 * | 6/2006 | Rabinoff et al. ............ 702/19 |
| 2009/0264734 A1 * | 10/2009 | Degani et al. ............ 600/420 |

FOREIGN PATENT DOCUMENTS

| | | |
|---|---|---|
| EP | 0 904 735 | 3/1999 |
| EP | 1 270 043 | 1/2003 |
| EP | 1 479 403 | 11/2004 |
| WO | WO 91/14186 | 9/1991 |
| WO | WO 91/18552 | 12/1991 |
| WO | WO 97/40871 | 11/1997 |
| WO | WO 98/07367 | 2/1998 |
| WO | WO 99/06849 | 2/1999 |
| WO | WO 00/71169 | 11/2000 |
| WO | WO 01/67979 | 9/2001 |

(56) References Cited

FOREIGN PATENT DOCUMENTS

| WO | WO 01/85230 | 11/2001 |
|---|---|---|
| WO | WO 02/061371 | 8/2002 |
| WO | WO 2007/023408 | 3/2007 |

OTHER PUBLICATIONS

Basser, "Interstitial Pressure, Volume, and Flow during Infusion into Brain Tissue", Microvascular Research, pp. 143-165, 1992.*
US 6,498,128, 12/2002, Abraham et al. (withdrawn).
R.H. Thomlinson et al.,: "The Histological Structure of Some Human Lung Cancers and the Possible Implications for Radio-Therapy", Br. J. Cancer, Vo. 9, pp. 539-549 (1955).
William Negendank, "Studies of Human Tumors by MRS: a Review", NMR in Biomedicine, vol. 5, pp. 303-324 (1992).
Janna P. Wehrle et al., "P NMR Spectroscopy of Tumors in Vivo", Cancer Biochem Biophys, vol. 8, pp. 157-166 (1986).
W. Michael Zawada et al., "Somatic Cell Cloned Transgenic Bovine Neurons for Transplantation in Parkinsonian Rats", Nature Medicine, vol. 4, No. 5, pp. 569-574 (1998).
George N. Phillips, Jr., "Structure and Dynamics of Green Fluorescent Protein", Current Opinion in Structural Biology, vol. 7, pp. 821-827 (1997).
Peter J. Basser, "Interstitial Pressure, Volume, and Flow During Infusion into Brain Tissue", Microvascular Research, vol. 44, pp. 143-165 (1992).
Judah Folkman et al., "Angiogenic Factors", Science, vol. 235, pp. 442-447 (1987).
Rakesh K. Jain, "Determinants of Tumor Blood Flow: A Review", Cancer Research, vol. 48, pp. 2641-2658 (1988).
Joanne R. Less et al., "Interstitial Hypertension in Human Breast and Colorectal Tumors", Cancer Research, vol. 52, pp. 6371-6374 (1992).
P. Falk, "Differences in Vascular Pattern Between the Spontaneous and the Transplanted C3H Mouse Mammary Carcinoma", Eur. J. Cancer Clin Oncol., vol. 18, No. 2, pp. 155-165 (1982).
N. Joan Abbott, "Evidence for Bulk Flow of Brain Interstitial Fluid: Significance for Physiology and Pathology", Neurochemistry International, vol. 45, pp. 545-552 (2004).
F.A. Howe, "Proton Spectroscopy In Vivo", Magnetic Resonance Quarterly, vol. 9, No. 1, pp. 31-59 (1993).
J. Ruohonen et al., "Focusing and Targeting of Magnetic Brain Stimulation Using Multiple Coils", Medical and Biological Engineering and Computing, vol. 35, No. 3, pp. 297-301 (1998).
Robert P. Adamski et al., "Solute Concentration Effect on Osmotic Reflection Coefficient", Journal of the Biophysical Society, vol. 44, pp. 79-90, (1983).
Paul S. Tofts et al., "Measurement of the Blood-Brain Barrier Permeability and Leakage Space Using Dynamic MR Imaging. 1. Fundamental Concepts", Magnetic Resonance in Medicine, vol. 17, pp. 357-367 (1991).
David S. Tuch.et al., "Conductivity Tensor Mapping of the Human Brain Using Diffusion Tensor MRI", Proceedings of the National Academy of Sciences, vol. 98, No. 20, pp. 11697-11701 (2001).
Roy O. Weller et al., "Cerebral Amyloid Angiopathy: Accumulation of Aβ in Interstitial Fluid Drainage Pathways in Alzheimer's Disease", Annals of the NY Academy of Sciences, vol. 903, pp. 110-117 (2000).

Thomas E. Yankeelov et al., "Quantitative Pharmacokinetic Analysis of DCE-MRI Data Without an Arterial input Function: a Reference Region Model", Magnetic Resonance Imaging, vol. 23, pp. 519-529 (2005).
E.T. Zhang et al., "Interrelationships of the Pia Mater and the Perivascular (Virchow-Robin) Spaces in the Human Cerebrum", Journal of Anatomy, vol. 170, pp. 111-123 (1990).
Lydia Vargova et al., "Diffusion Parameters of the Extracellular Space in Human Gliomas", GLIA, vol. 42, pp. 77-88 (2003).
M. Wintermark et al., Comparative Overview of Brain Perfusion Imaging Techniques, Stroke, vol. 36, pp. e83-e99 (2005).
Carol P. Geer et al., "Interstitial Fluid Flow Along White Matter Tracts: A Potentially Important Mechanism for the Dissemination of Primary Brain Tumors", Journal of Neuro-Oncology, vol. 32, pp. 193-201 (1997).
A. Giese et al., "Cost of Migration: Invasion of Malignant Gliomas and Implications for Treatment", Journal of Clinical Oncology, vol. 21, No. 8, pp. 1624-1636 (2003).
Rakesh K. Jain, "Transport of Molecules Across Tumor Vasculature", Cancer and Metastasis Reviews, vol. 6, pp. 559-593 (1987).
Edwin N. Lightfoot et al., "Hydrodynamic Models for Diffusion in Microporous Membranes", Annals of Biomedical Engineering, vol. 4; pp. 78-90 (1976).
C.C. Michel et al., "Microvascular Permeability", Physiological Reviews, vol. 79, No. 3, pp. 703-761 (1999).
H. Pollock et al., "Perivascular Spaces in the Basal Ganglia of the Human Brain: Their Relationship to Lacunes", Journal of Anatomy, vol. 191, pp. 337-346 (1997).
Paul S. Tofts et al., "Modeling Tracer Kinetics in Dynamic Gd-DTPA MR Imaging", Journal of Magnetic Resonance Imaging, vol. 7, No. 1, pp. 91-101 (1997).
Paolo A. Netti et al., "Macro- and Microscopic Fluid Transport in Living Tissues: Application to Solid Tumors", American Institute of Chemical Engineering, vol. 43, No. 3, pp. 818-834 (1997).
Paolo A. Netti et al., "Role of Extracellular Matrix Assembly in Interstitial Transport in Solid Tumors", Cancer Research, vol. 60, pp. 2497-2503 (2000).
English language abstract of EP 1 270 043, published Jan. 2, 2003.
International Preliminary Report on Patentability issued in International Application No. PCT/US2008/062922, mailed Dec. 3, 2009.
James G. Berryman et al., "Microgeometry of Random Composites and Porous Media", 19 pages (1988).
International Search Report issued in International Application No. PCT/US08/62922, mailed Nov. 25, 2008.
Written Opinion issued in International Application No. PCT/US08/62922, mailed Nov. 25, 2008.
Ian R. Porteous, "Geometric Differentiation: for the Intelligence of Curves and Surfaces, Second Edition", pp. i-xv and 1-333, Cambridge University Press (2001).
John H. Byrne et al., "An Introduction to Membrane Transport and Bioelectricity, Second Edition", pp. i-ix, and 1-198, Raven Press (1994).
Rosemary D. Bevan et al., "The Human Brain Circulation: Functional Changes in Disease", pp. i-xiv, and 1-456, Humana Press (1994).
Fitz-Roy E. Curry, "Chapter 8: Mechanics and Thermodynamics of Transcapillary Exchange", Handbook of Physiology, Section 2: The Cardiovascular System, pp. 309-374 (1984).
Yuna-Cheng Fung, "Biomechanics: Motion, Flow, Stress and Growth", pp. i-xv, and 1-569, Springer-Verlag (1990).

* cited by examiner

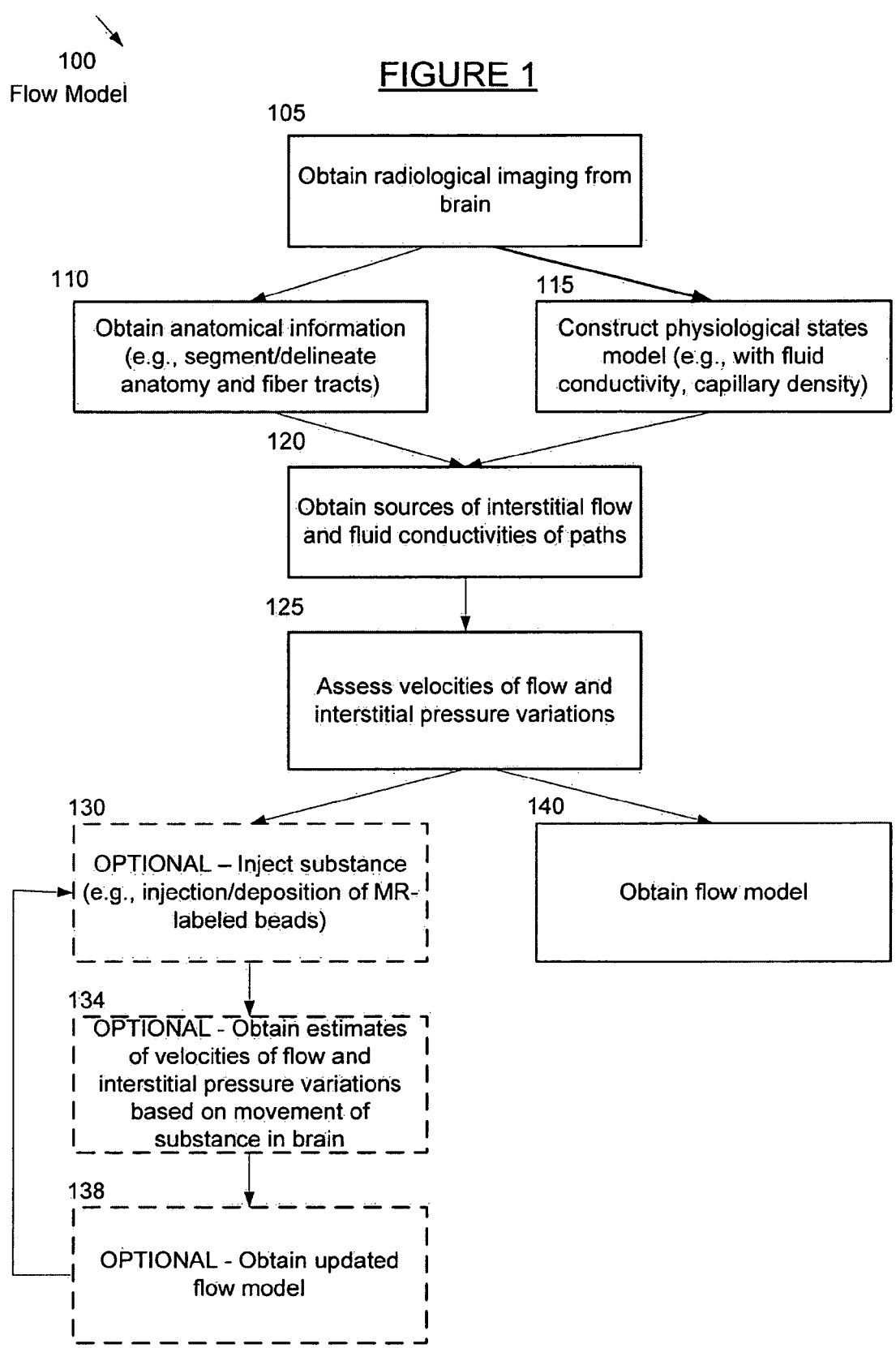

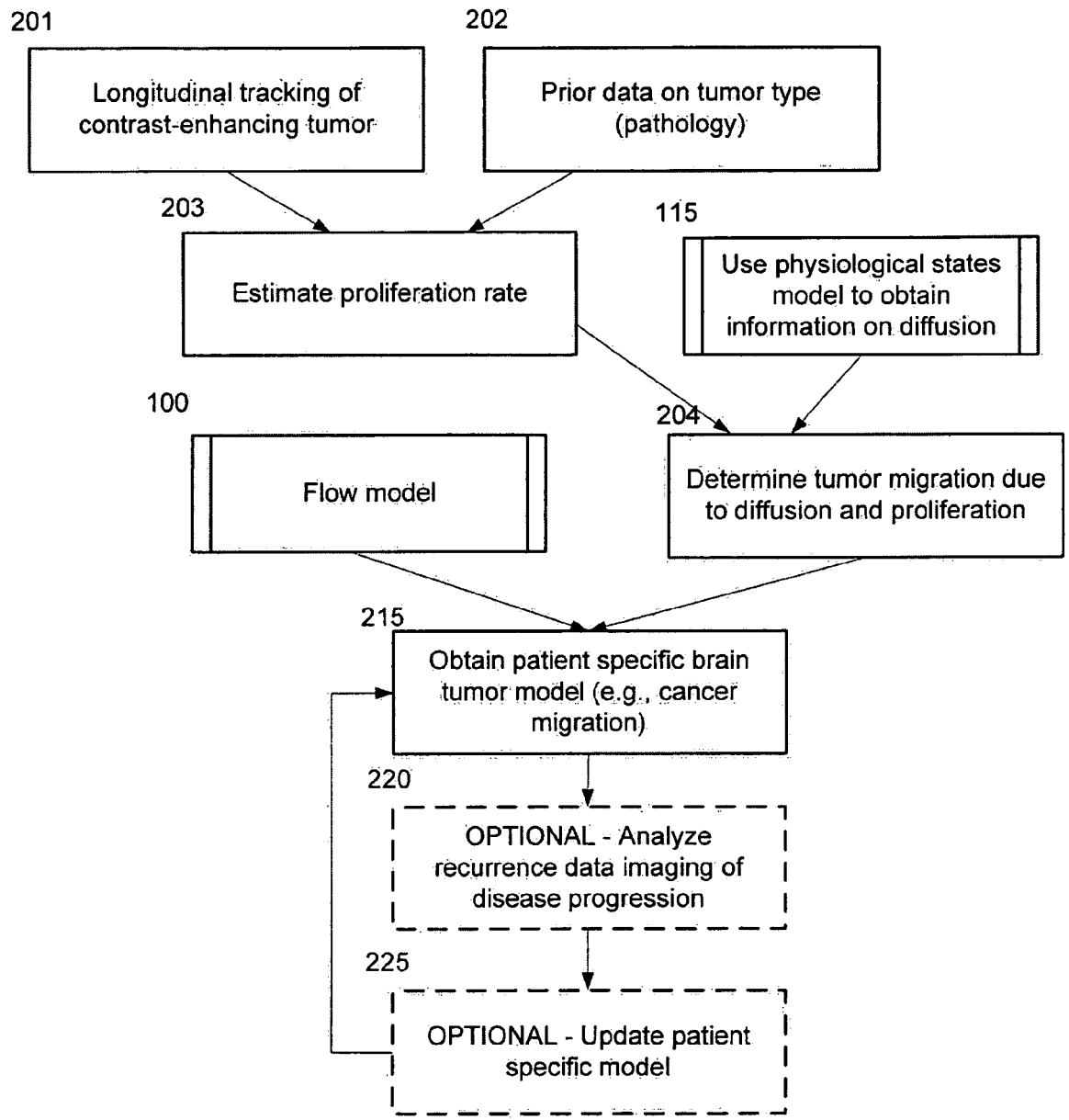

- expand radiosurgical target area
- combine radiosurgery and targeted drug delivery

METHODS AND SYSTEMS FOR PROVIDING PLANNING AND DISPENSATION OF RESEARCH AND/OR TREATMENT FOR BRAIN DISEASE

This application claims priority to Provisional Patent Application No. 60/938,863, filed on May 18, 2007, and entitled "A Treatment Simulator For Brain Diseases And Method Of Use Thereof", which is herein incorporated by reference.

FIELD OF THE INVENTION

The present invention relates to the field of physiology, diagnostics, monitoring, and treatment.

BRIEF DESCRIPTION OF THE FIGURES

FIG. 1 illustrates a flow model for assessing velocities of flow and interstitial pressure variations, according to one embodiment.

DETAILED DESCRIPTION OF THE EMBODIMENTS OF THE INVENTION

A system and method is illustrated for providing more information at the point of care for effective planning and dispensation of treatment for brain diseases. The pathways into the brain are often, the paths of ingress of chemotherapeutic molecules entering the brain, as well as the paths of egress of such molecules leaving the region in the brain where they are needed. Likewise, the pathways within the brain are the routes of migration of primary brain cancer cells, of advection of plaque in Alzheimer's disease, of serum proteins from disrupted blood-brain barrier in diseases, of endogenous flow dictating the long term migration of therapeutic particles, and other important phenomena in health and sickness. Information on these pathways and their function help in a variety of brain disorders, and also'help estimate how chemotherapeutic and other particles distribute from, and along, these pathways.

System for Treating Brain Disease

Figure 1A:
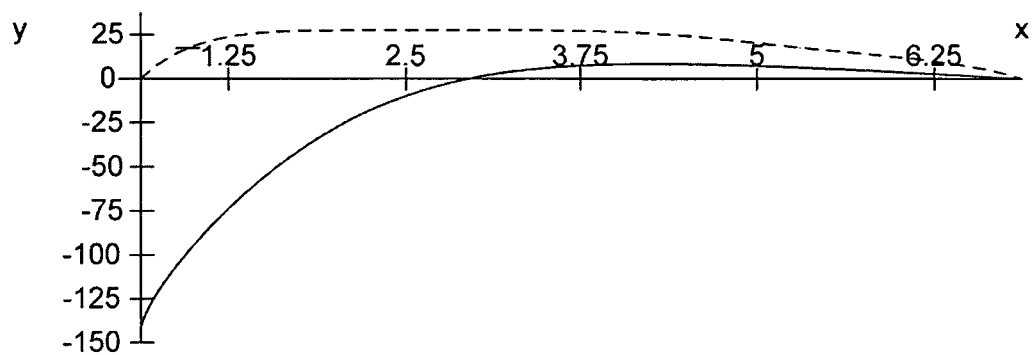
FIGS. 1A-1B illustrate pressures and velocities used in an example of a flow model construction, according to one embodiment.
Figure 1B:
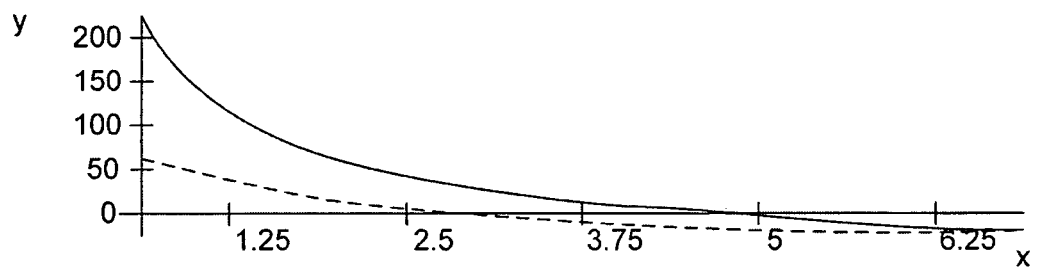
Figure 1C:
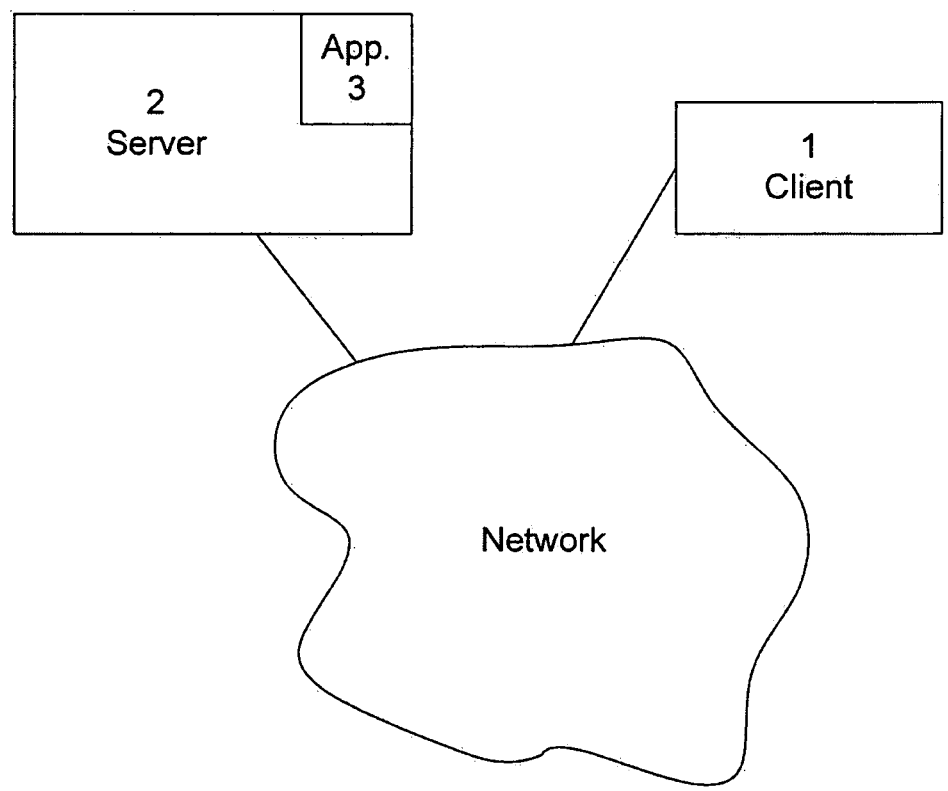
FIG. 1C-1D illustrate a system for providing information for treating brain disease, according to one embodiment.

FIG. 1C illustrates a system for treating brain disease, according to one embodiment. Client computer 1 is connected to server computer 2 by a network. Server computer 2 has an application 3 which helps provide information to treat brain disease. Note that, in one embodiment, application 3 is part of or connected to server computer 2. However, in some embodiments, application 3 may be connected to server 2 by the network.

Figure 1D:
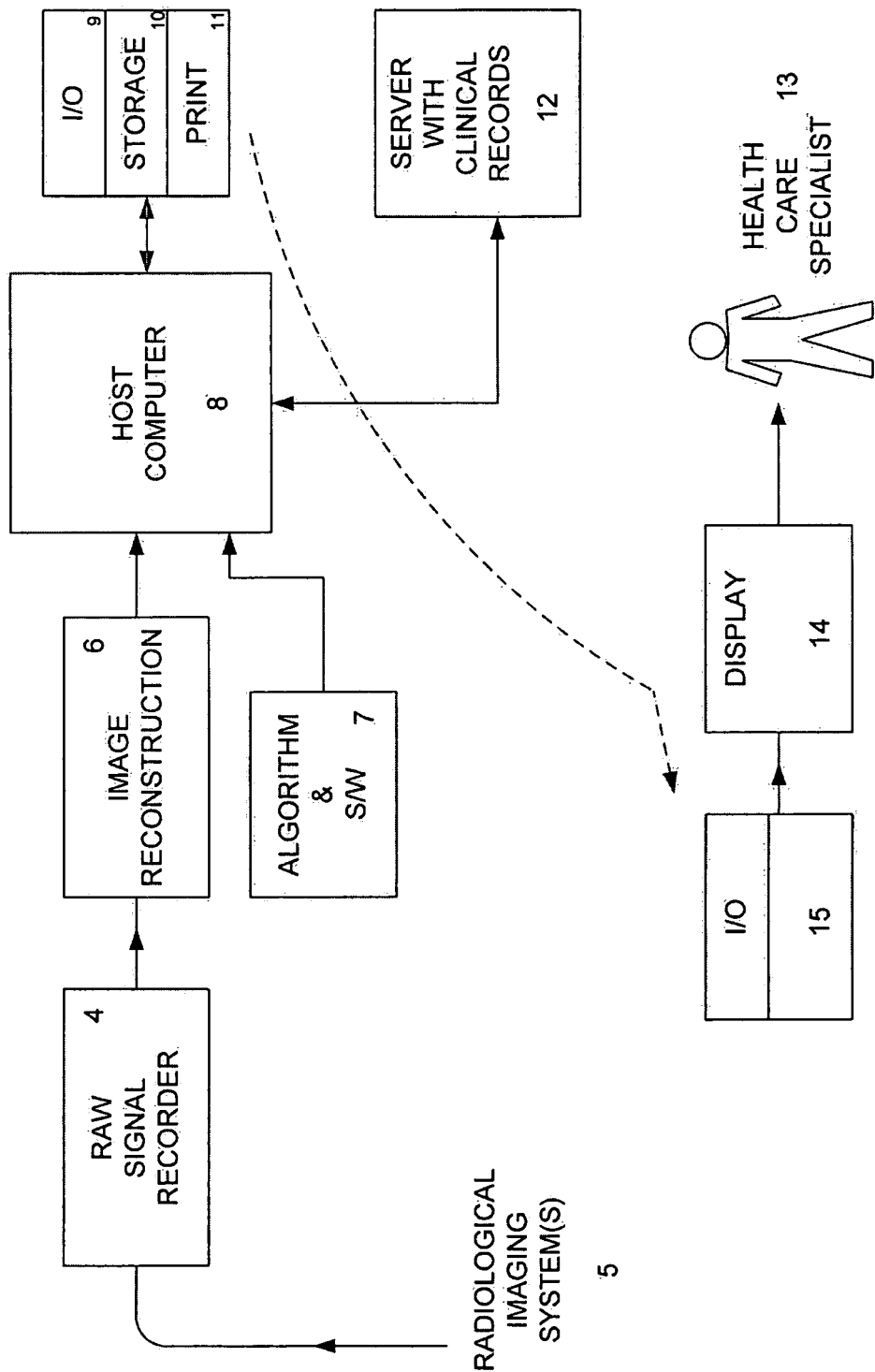

FIG. 1D illustrates details of how application 3 functions, according to one embodiment. Radiological imaging is collected on a patient using a radiological imaging system 5. Possible radiological imaging systems can include MRI, positron emission tomography (PET), imaging of radioactive labels in chemotherapeutic molecules, CT, etc. A raw signal recorder 4 can record the raw signals available from the radiological imaging system 5 so that the raw signals can be reconstructed by an image reconstruction system 6 and put to use. This is optional and can improve the performance of the system in some embodiments, but is not necessary. The algorithms 7 can be reduced to software and compiled or interpreted on the host computer and thus car run on the radiological imaging data. The host computer 8, can be a computer associated with the imaging system itself, a laptop, the workstation in the physician's office, or even computers in a remote location (e.g., used when the work is outsourced). The computer 8 can have interface 9, storage, 10 and print capabilities 11. Retrospective data 12, such as individual patient relevant clinical records, other imaging data, or statistical data collected on similar patients, etc., can also be utilized by the computer 8, in some embodiments. The user interfaces 15' and displays 14 of models can then be used by appropriate users (e.g., specialists).

Treatment of Brain Disease

Figure 1E:
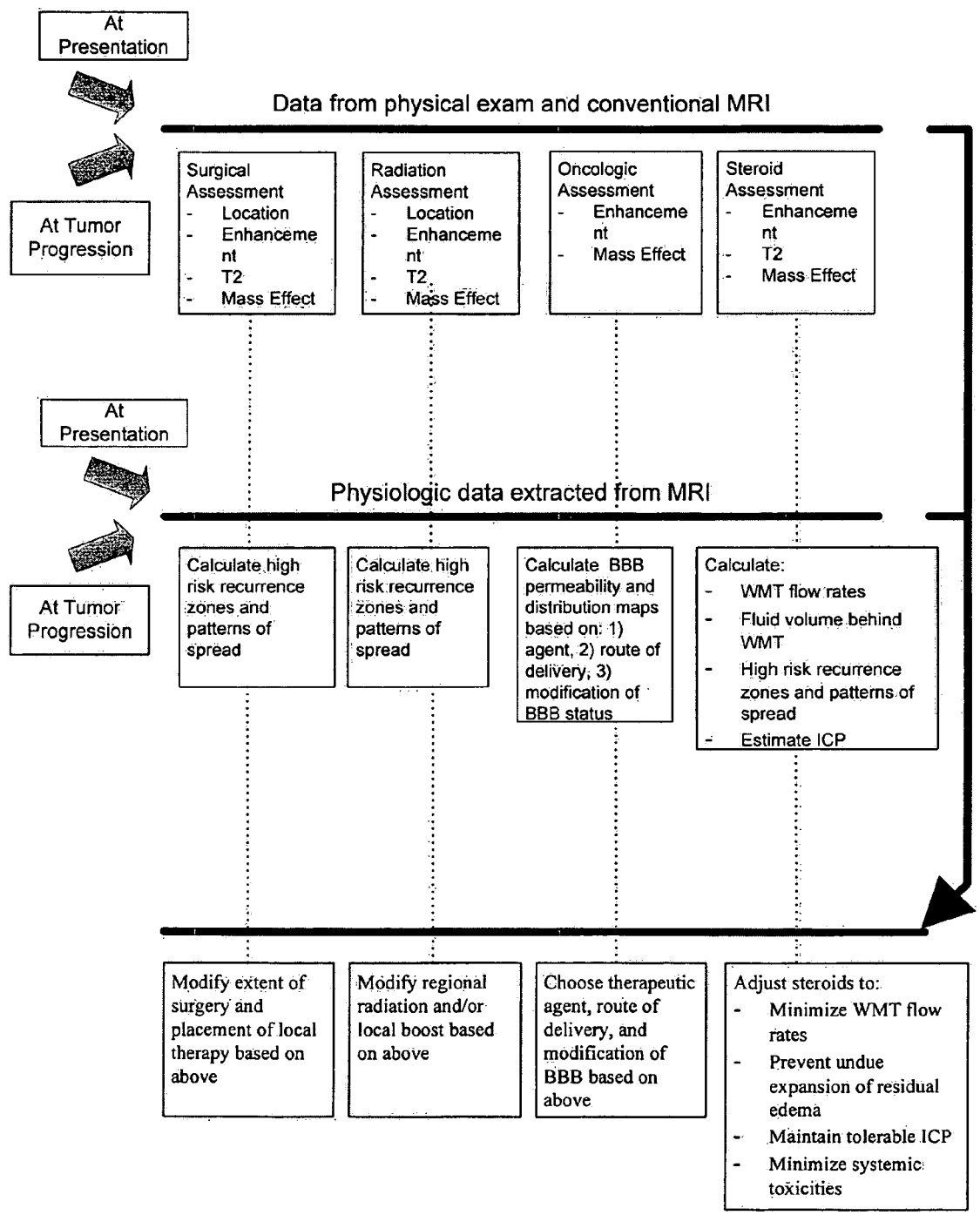
FIG. 1E illustrates various treatment plans for brain disease, according to several embodiments.

FIG. 1E describes various treatment plans of brain disease, according to several embodiments of the invention. The top row illustrates the assessment needs for four example decision routes that physicians choose amongst, namely surgery, radiation therapy, chemotherapies following an assessment of the state of a cancer (oncological), and ancillary therapies, such as steroid treatments. New assessments can be made that can modify decision routes, both in terms of their timing and their extent. Examples of these are described for each of the decision groups below. Those of ordinary skill in the art will see that many other decision routes and assessments can be made.

Surgery.

Neurosurgeons can use the history, physical examination, and conventional information from magnetic resonance imaging (MRI) scans to determine the location, contrast enhancement, amount of edema and mass effect to decide on their surgical procedure. Information can also be provided on high risk recurrence zones, likely toxicities of surgery, and likely patterns of spread that is not conventionally available. This can shape their decisions on how to approach surgery and whether local therapies should be considered intraoperatively.

Radiation.

Radiation oncologists can use the history, physical examination, and conventional information from MRI scans to determine the location, contrast enhancement, amount of edema and mass effect to decide on their planned radiation therapy. Information can also be provided on high risk recurrence zones, likely toxicities of radiation therapy, and likely patterns of spread that is not conventionally available. This can shape their decisions on how to design their overall radiation fields and their decisions on the region to boost with additional external beam or interstitial radiation.

Medical Oncology.

Medical oncologists can use the history, physical examination, and conventional information from MRI scans to determine the dimensions of a contrast enhancing tumor and the amount of edema and mass effect in planning permeability and drug distribution maps based on: 1) the agent (e.g., molecular weight and lipid solubility), 2) route of delivery (e.g., systemic [e.g., intravenous or intraarterial] or interstitial [e.g., convection enhanced delivery (CED) or polymeric delivery]), and 3) potential changes to the integrity of the blood brain barrier (BBB) (e.g., change in steroids, post-RT, intra-arterial mannitol, etc). This physiologic information can affect clinical decisions on the use of pharmacologic agents in these diseases.

Ancillary Therapies.

Steroids, such as glucocorticoids, can be used as therapy for peritumoral brain edema and work by altering the integrity of the blood brain barrier. If the BBB is markedly disrupted large amounts of plasma proteins enter the brain osmotically bringing water with them. This causes an increase in the flow of fluids down white matter tracts which may further disseminate these tumors with the central nervous system. In addition, once these white matter tracts are overloaded, extracellular fluid backs up in the region of the leaky BBB causing mass effect, increased Intra-Cerebral Pressure (ICP) and symptomatic deterioration. While high doses of glucocorticoids would be advantageous for the reasons listed above, they can cause serious systemic toxicities. Physiologic parameters can provide unique information to make rationale decisions to minimize steroid doses (such as glococorticoids) while monitoring WMT flow rates and amounts of edema, potentially reducing the intracranial dissemination of these cancers.

Another example of an ancillary therapy is plaque dissolving therapy. Alzheimer's disease is one where plaque can form in the neocortex, due to clumping of the mutated amyloid beta protein. The nearest Cerebral Spinal Fluid (CSF) spaces tend to be the perivascular or Virchow-Robin spaces, and thus the flow of interstitial fluid here tends to accumulate the plaque in these spaces. A map of the fluid pathways that are in the cortex can give the physician the most likely points of accumulation of plaque, and thus the target regions for plaque-dissolving therapies.

Other ancillary therapies that can be used include the distribution of cytokines for directing stem cell migration in brain parenchyma, and a simulator for drug delivery for pharmaceutical industry applications. Some examples of these will be described in further detail below.

Construction of the Treatment Simulator

One component of a treatment simulator is the construction and embodiment of a model for endogenous flow of interstitial fluid (ISF) in the brain. FIG. 1 illustrates the basics in the construction of such a flow model, which assists in therapeutic decisions as described in FIG. 1, according to one embodiment. First, one or more radiological images are taken (105). These include but are not limited to diffusion tensor imaging with for example, a so-called σ value of 1000 that allows us to delineate the directionality of the white matter fiber tracts; and a T1-weighted SPGR (spin spoiled gradient recalled echo sequence) proton density imaging protocol and/or a dual-echo T2 weighted image for the same purpose. (These acronyms are well known in the field of magnetic resonance (MR) imaging.) In combination with the diffusion tensor image, this allows us to construct a map of the extracellular volume fraction, which is of particular interest in brains with injury such as trauma, or stroke, or disease, such as brain cancer, or Alzheimer's. Further imaging that could be taken include dynamic contrast enhanced (DCE) imaging with either MR or CT (computed tomography) visible contrast agents that allow us to construct maps of (i) the plasma fluid filtration rate, (ii) the capillary density or (iii) the BBB permeabity to water-soluble molecules of size similar to that of the contrast agent used. The filtration rate and the capillary density allow us to construct both a source strength and source density for endogenous fluid flow in the brain. Thus from these and other images, we can deduce the physiological parameters (115) and their spatial locations (overlay with 110) that provide the constitutive and source terms in a mathematical model for bulk flow of interstitial fluid in the brain (120). In 125, the mathematical model computes the intracranial pressure distribution and the fluid flow pathways and velocities from a combination of D'Arcy's law for fluid flow in a porous medium and the conservation of mass of fluid (allowing for the capillary sources including ones that arise on account of the damaged BBB in brains with disease or injury). In 140, the model flow is obtained. This is discussed in more detail below.

In one embodiment, direct experimental construction of bulk flow pathways in an individual brain can be provided (130, 134, 138). In 130, a magnetic resonance contrast agent such as beads encapsulated with iron particles, or emulsion particles with a coating of Gadolinium (those skilled in the art will know of other possibilities, as well as use of other imaging modalities, such as the use of contrast reagents for computed tomography (CT) can be deposited at particular parts of the brain, and tracked for periods of time. In 134, by suitable choice of size of particles, and of the magnetic moment encapsulated within or distributed on the surface, one can map the flow velocities which convect the beads, without the confounding issue of diffusive or other transport. In 138, such experimental construction can also be used to improve, refine, or update the flow model. We now describe below an approach to the construction of the mathematical model mentioned in the preceding paragraph.

Mathematical Model for Bulk Flow.

Herein, we describe some mathematical approaches to modeling the bulk flow pathways, and for obtaining the patient-specific parameters to implement the model for a particular living brain. Since the concentrations of various types of particles will be referred to, we summarize our notation:

| Symbol for particle concentration | Particle type |
|---|---|
| c | Serum proteins, principally albumin |
| m | Contrast reagent for perfusion imaging |
| n | Chemotherapeutic molecule |

In a normally functioning, intact brain there is production and removal of interstitial fluid. It is generally agreed that the sources of fluid are the vasculature and capillaries. The sinks are the CSF spaces (e.g., the ventricles, the perivascular, and the periarterial spaces). The additional fluid pumped into the brain due to a growing tumor and the attendant edema can have importance in tumor migration.

The source of interstitial fluid is generally accepted to be the capillary system in the brain. Kinetic equations for transport across a membrane yield a production rate for fluid per unit volume of tissue according to $$\nabla \cdot v_i = q := \frac{L_p S}{V}((p_v - R\Pi_v) - (p - R\Pi)) \quad \text{(Equation 1)}$$

Note that := means that the quantity facing the colon is defined to be the quantity facing the equality sign.

$$\frac{L_p S}{V}$$

is the capillary hydraulic conductivity per unit tissue volume. The $v_i$ is the interstitial velocity. The p's are hydrostatic pressures inside the capillaries (subscript v) or in the interstitial space (no subscript). The q is the interstitial production rate. The Π are the corresponding osmotic pressures of blood plasma proteins (e.g., albumin). R is called the osmotic reflection coefficient[1] and has a microscopic interpretation that relates it to the equilibrium albumin concentrations inside and outside the vessel. Phenomenologically, R measures the departure of the vessel walls from semi permeability with R=1 being impenetrable to the albumin or solute in question, and R=0 being open to the diffusive transport of both solute and solvent molecules. Active transport of molecules across the wall as well as transport of ions with the accompanying electrical phenomena such as voltages across the membrane will require further considerations. Equation (1) can be combined with D'Arcy's law, extended to include osmotic pressure

[1] It is usually denoted by a but we reserve this letter for the Cauchy stress.

$$v_i = -K\nabla(p-\Pi) \quad \text{(Equation 2)}$$

so that we may begin to discuss how to solve for the bulk flow pathways. (Note that K is the hydraulic conductivity.) Substituting from D'Arcy's law into Equation (1) results in one equation for two unknown functions of space: p and Π.

Endogenous Bulk Flow in Normal Brain.

Let us consider a normal, intact brain. We can for example take the intravascular pressure, the osmotic pressures, the hydraulic conductance of the capillary wall, and the reflection coefficient to all be fairly uniform. The intravascular pressures can range from an average of close to 100 mm of Hg in the middle cerebral artery down to below 20 mm in the arterial capillaries. Below, for purely illustrative purposes, we will assume a uniform distribution of the capillaries per unit volume of tissue as well. Later we describe how to obtain this and other parameters specific to an individual to construct an individualized bulk flow map. The right hand side of Equation (1) must be positive for there to be an influx of fluid from blood vessels to the interstitium.

Illustrative Analytic Examples.

Let us first consider a homogeneous, isotropic, spherical brain. We regard the outer surface of the brain to be a sphere of radius b, while the ventricles are considered an inner sphere of radius a<b. Taking all parameters to be homogeneous and isotropic, so that in particular the tensor field of the hydraulic conductivity is a single number k, we get from D'Arcy's law, $$\nabla^2 p = -\tilde{q} =: -\frac{\overline{q}}{\phi k} \quad \text{(Equation 3)}$$

Replacing the Laplacian by the form it takes in radial coordinates r $$\frac{1}{r^2}\frac{d}{dr}\left(r^2\frac{dp}{dr}\right) = -\tilde{q} \quad \text{(Equation 4)}$$

The general solution to this is $$\frac{p(r)}{c} = -\frac{A}{r} - r^2 + B$$

$$\frac{p'(r)}{c} = \frac{A}{r^2} - 2r \quad \text{(Equations 5, 6, 7)}$$

$$c := \frac{\tilde{q}}{6}$$

(Note that A and B are constants of integration.) The most natural boundary condition is to assume that the CSF in the ventricles and in the sub-arachnoid space is at a constant pressure, which we take to be the reference or zero pressure:

$$p(r=a)=0=p(r=b) \quad \text{(Equation 8)}$$

If, however, we assume that the interstitial fluid drainage is all through the ventricles and not through the pial surface into sub-arachnoid space, the boundary condition would be of the form $$v_r|_{r=a}=\text{given}$$

$$p(r=b)=0 \quad \text{(Equations 9, 10)}$$

where $v_r$ is the radial influx speed into the ventricles. Using D'Arcy's law, and again assuming every portion of the inner surface is equally permeable to the fluid, this boundary condition is of the form:

$$\left.\frac{dp}{dr}\right|_{r=a} = \frac{q}{4\pi a^2} \times \frac{1}{\phi k} \quad \text{(Equation 11)}$$

Choose $$a = 1, b = \frac{1}{2}\sqrt{217} - \frac{1}{2} \approx 6.865.$$

(These radii will be in rough agreement with the ratio of the ventricular volume to brain volume. The choice for b can be for convenience.) The two curves in FIGS. 1A and 1B show the behaviors of the pressures and the velocities for the two different boundary conditions we have indicated. The larger pressure variations occur for the model where the flux is forced to be entirely into the 'ventricular' space in this model. Note that FIG. 1A illustrates pressures with different boundary conditions. FIG. 1B illustrates velocities (positives=radially inward).

Returning to computing the bulk flow pathways, we can do so provided we have an estimate for q, the interstitial production rate, as well as the hydraulic conductivity K over the region of the brain. This is because we are on fairly sure ground in assuming a uniform background of sources, in proportion to the specific volume of the functioning capillaries. We discuss obtaining these parameters later, and proceed with the case of brains with injury that results in edema, and a breakdown of the BBB.

Bulk flow pathways in edematous brain. As a prelude to discussing methods we could apply to an individualized brain, let us revisit the equations, but this time for a brain where there are disruptions of the BBB. In this case, at a minimum, we cannot neglect the variations of the reflection coefficient and the interstitial osmotic pressures. However, in the expression $$q = \frac{L_p S}{V}((p_v - R\Pi_v) - (p - R\Pi)) \quad \text{(Equation 12)}$$

we note the following: q itself may be obtained by certain contrast imaging techniques (see later). For the individual terms, the capillary conductance does not vary much: the disruption of the BBB is caused mostly due to the increased permeability of the capillary walls to the serum proteins (R≠1 where there is disruption). We need to estimate this reflection coefficient in different parts of the brain. However, again due to the capillaries being the primary source, we can assume approximately that $p_v - R\Pi_v$ varies primarily due to BBB disruption. However, we need now to account for the fact that the albumin has distributed over the intersitial space, having spilled out of regions of disruption. For this, we invoke the equation of flow of particles in the interstitial space (see above). Denoting the concentration of albumin in the interstitial space by c, and in the blood vessels by c and accounting for the source which produces this, we have, by making the simplification that the convective velocity of the protein in the interstitium is just that of the fluid, $$\frac{\partial c}{\partial t} = -\nabla \cdot (cv) + \nabla \cdot (D\nabla c) + q_c - a(c, p) \quad \text{(Equations 13, 14)}$$

$$q_c = \frac{PS}{V}(c_v - c) + q(1 - R)c_v$$

Note that t is time, and a(c, p) is a term that accounts for chemical reactions and metabolism. The expression for the transport of the solute into the interstitial space (Equation 14) is standard, but is somewhat simplified in the last term, where more nonlinear terms could be taken into account. Further, as the references show, it is a simplification to identify R with the osmotic reflection coefficient previously introduced. It can be more correctly identified with a different parameter called the solute drag coefficient or ultrafiltration coefficient. Mindful of the need for perhaps taking into account these more accurate theories, we proceed by using the simpler case as the exemplar. Substituting for $\nabla \cdot v$ from above, we get (only the case $R \neq 1$ is relevant for our example purposes)

$$\frac{\partial c}{\partial t} = -v \cdot \nabla c + \nabla \cdot (D\nabla c) + \left(\frac{PS}{V} + q\right)(c_v - c) - Rqc_v - k_d c \quad \text{(Equation 15)}$$

where we have replaced the complex biochemistry for albumin in brain parenchyma by an irreversible degradation rate, which is known from various studies. Note that $k_d$ is the degradation and loss of serum protein from interstitium. We need to solve the equation for the $\rho$, $\Pi$ simultaneously to derive the bulk flow pathways. The osmotic pressure is a defined function of the interstitial concentration, in the dilute limit it is just $$\Pi = kTc \quad \text{(Equation 16)}$$

where the concentration is the number of molecules per unit interstitial volume. (Note that T=temperature; k=Boltzmann's constant, and c=the concentration of serum protein in interstitium.) More exact expressions can be used if found necessary. Assuming we know the parameters (e.g., the hydraulic conductivity, functional capillary density, diffusivity, permeability, reflection coefficient, and degradation rate) we can reduce the pair of equations to completion, if we know $\rho_v$ and $\Pi_v$. We can assume these to be fairly constant. Then, we have a pair of partial differential equations, equations (1) and (15), that need to be solved simultaneously. We have displayed only the steady-state equation for the fluid velocity; since in many circumstances we encounter the brain somewhat after disease, such as when cancer has taken hold, and the period of our observation can be fairly short, we can also look just at the steady state version of the concentration equation where the right hand side of (Equation 13) can be set to zero. The boundary conditions on the hydrostatic pressure are given at the interfaces between the parenchyma and the cerebrospical fluid (the ventricles and the arachnoid granulations), reducing to the measurable and known CSF pressure there. The initial/boutindary conditions on the albumin concentration flux can be assumed to be proportional to the $$\frac{PS}{V},$$

or to $$\frac{PS}{V} + q,$$

and to go to zero at the outer edges due to reabsorption and degradation. This then is an approach to solving for the bulk flow pathways in the presence of edema and disease. A review of the approaches to the parameter estimation is given in that the next section.

Parameter Estimation.

In order to solve the equations for a particular individual, we have to estimate several parameters. We list these in the table below, and then discuss the imaging methodologies which allows us to estimate the parameters. All parameters belonging to an imaging methodology are discussed under that rubric. For brevity, we discuss one method for obtaining each of the parameters: there are other potential methods which we do not list or discuss which will be apparent to those of ordinary skill in the art.

| Symbol | Meaning | How obtained |
|---|---|---|
| φ | connected extracellular fluid volume fraction | Proton density imaging |
| v | fluid velocity field relative to tissue | Solved via D'Arcy's law |
| q | rate of production of interstitial fluid | DCE |
| K | hydraulic permeability | DTI |
| p | hydrostatic pressure relative to a resting pressure in tissue | Solved for |
| c | concentration of serum protein in interstitium | Solved for |
| Π | osmotic pressure of serum protein in interstitium | constitutive relation to c |
| D | extracellular diffusion tensor of serum protein in interstitium | DTI |
| $k_d$ | degradation and loss of serum protein from interstitium | Assumed/estimated |
| R | reflection coefficient for serum protein from capillary walls | DCE |
| $\frac{PS}{V}$ | Permeability-area product per unit tissue volume for serum protein | DCE |
| $\frac{L_p S}{V}$ | Capillary hydraulic conductivity | DCE |

Proton Density Imaging.

We estimate the pore or extracellular volume fraction from proton densities. Proton density or other imaging can give us the water fraction. To convert the water fraction to an extracellular volume fraction, we need to know the fraction of the volume that contains water. The extracellular volume fraction is arrived at following anatomic imaging that delineates grey matter, white matter, CSF spaces, etc. and assigning nominal values known from the literature related to these regions. The proton density image then allows us to compute the extracellular volume by observation of the current proton density.

Perfusion and Dynamic Contrast-Enhanced Imaging (DCE).

All of the parameters obtainable from DCE are done with a time-series analysis following bolus injection. Although, there are many methods for examining transcapillary transport, for example purposes we focus on MR- and CT-based dynamic contrast enhanced imaging. A two-compartment model for DCE imaging models the rate at which the contrast agent (with concentration here denoted by m for marker) is the short time version of the equation used for the albumin concentration above, but with parameters appropriate to the contrast agent:

$$\phi \frac{dm}{dt} = \frac{PS_m}{V}(m_v - m) + q(1 - R_m)m_v \quad \text{(Equation 19)}$$

where m is the interstitial concentration of the tracer, $PS_m$ is the permeability-area product per unit tissue volume of the blood vessels to the tracer, $R_m$ is the reflection coefficient discussed above, but now for the tracer molecule (the suffix is appropriate when it is a Gadolinium chelate), and $m_v$ is the concentration of the tracer molecule within the blood vessels. q has exactly the same meaning as above, namely the rate per unit tissue volume, at which fluid is being pumped out of the blood vessels into the interstitium in the brain which has been invaded by tumor, but not yet by CED interventions. (This is called the filtration rate of the plasma fluid.) The first term on the right hand side is the diffusive transport of the tracer, the second the convective transport. Again this equation applies at every spatial location (voxel) in the brain. There is of course a second equation for the plasma or blood vessel concentration of the contrast agent:

$$\phi_v \frac{dm_v}{dt} = F(m_A - m_v) - \frac{PS_m}{V}(m_v - m) \quad \text{(Equation 20)}$$

The variable $m_A$ is called the arterial input function, and is either known, or allowed for. F is related to the regional cerebral blood flow. Following an injection of a bolus of the contrast agent by imaging, one can, from a time-series analysis, fit the parameters to obtain the parameters above, as well as the functional, capillary density (related to the integrated signal overtime) wherever there is signal.

Diffusion Tensor Imaging.

Diffusion tensor imaging can be used in various ways to obtain hydraulic conductivity and the diffusion of large molecules.

In FIG. 2, we show a comprehensive tumor dissemination model, wherein diffusion (including the convective component of diffusion that varies spatially) and proliferation are included to provide a risk map for recurrence. This map can be overlaid on anatomic, surgical, or radiation therapy planning maps to provide the physician with further information, as has been discussed in conjunction with FIGURE A above. In addition to the bulk flow dissemination of tumors (obtained from 100 as discussed for FIG. 1), additional information is obtained both from the prior data (e.g., biology) of the tumors (202) which can give indications of the proliferation rate either in-vitro or, from biopsies, a certain amount of in-vivo information can be added. Since biopsies are not routinely repeated, estimates from a combination of (i) longitudinal contrast imaging (201) which gives crude estimates of proliferation rates when the tumor mass is substantial enough to be visible in contrast-enhance MR, and (ii) biologic information about the proliferation rate of the tumor cells (202), and (iii) any further quantization obtainable from estimates of the fraction of tumor stem cells within given masses of tumor (204), can all be used to estimate the proliferation rate in-vivo (203). Further, the different methods will give us quasi-independent estimates which can then be compared for consistency. A model that combines bulk flow (100), diffusion (115), and proliferation (203) can then be constructed, and a patient-specific model of cancer growth and migration (215) can then be offered the physician. This model has the advantage that the different mechanisms of cancer spread can be turned on or off in the simulations giving a spread of recurrence estimates from the worst case to the less ominous. The model and its parameters can be updated (225) on a continual basis based on observations and imaging of the patient (220) to provide a current best estimate tumor dispersal map for planning of therapies.

Primary brain tumors are unlikely to spread distally by proliferation. Thus, the model will likely account for the spread due to bulk dissemination alone. If proliferation data is available and considered important, these can be used. We point out that in the presence of edema, such as in brain tumors and in injury, the influence of increased extracellular volume fractions is profound. We illustrate this below.

The expansion of the extracellular space can greatly facilitate transport of large particles such as glial tumor cells. For purely illustrative purposes, consider a square lattice with lattice points spaced by $d \geq 2$, with circles of radius unity drawn at the lattice points, the area fraction of the lattice not enclosed within the circles is $$\phi = 1 - \frac{\pi}{d^2} \quad \text{(Equation 17)}$$

(so that when the circles are just touching, $\phi \approx 0.215$). Then the radius $\rho$ of the circle that can be accommodated within the 4-cusped regions outside the circles is $$\rho = \sqrt{\frac{\pi}{2(1-\phi)}} - 1 \quad \text{(Equation 18)}$$

Figure 2A:
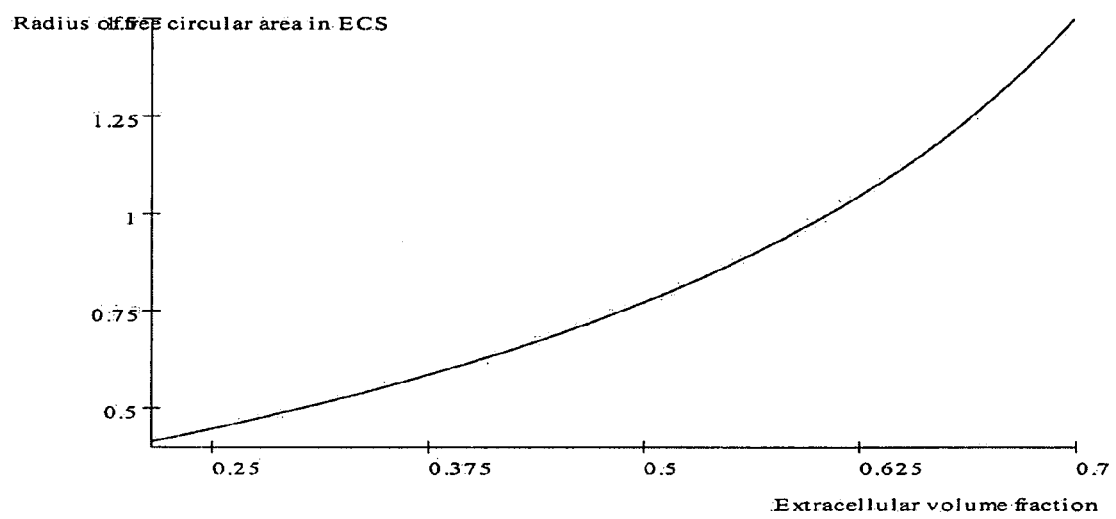
FIGS. 2-10 illustrate various methods of providing information for treating brain disease, according several embodiments.

The size (radius) of this circle increases from about 0.41 for the closely packed case, when the originally considered circles just touch to about 1.5 when the volume fraction increases to 0.75. If the radius of the original circles (the width of a myelinated axon for example) is about 2 microns then the curve below suggests that a cell of radius about 1.5 times that, or about 3 microns can pass freely through the interstitial spaces at volume fractions of 0.75. Such volume fractions are of the order of magnitude of what has been observed in porcine brains, and can be expected to occur in humans. Of course, cells being distensible do not need free passage to make it through interstitial spaces in even a passive way. The movement of distensible cells can be estimated through methods involving extensional shear and associated forces that push the cells along the pathways of the flow of the fluid. FIG. 2A illustrates a radius of free circular area in extracellular space (ECS) versus extracellular volume. Thus, when the brain is under normal conditions, the extracellular volume fraction is at the origin of the abscissa, i.e. about 20% of the volume of, say tissue in white matter, is extracellular. If we take the radius of an axon or fiber in this space at 1 micron, then the spaces between axons, in the directions of the fibers can accommodate a sphere of at most about 0.45 microns (the intercept of the curve with the ordinate). However, when, as is the case with tumor-induced edema, the extracellular volume fraction can roach 70% or so, then the sphere that can be accommodated (say a cancer stem cell or cancer cell without appendages) can be well over a micron in radius, an increase of a factor of 3 in the linear dimension of the particle that can be accommodated, and that can be transported without undue hindrance or need for distension of the cellular particle. Since cells are quite distensible, this further increases the size of the particles that can be transported due to the convection of ISF.

Figure 3:
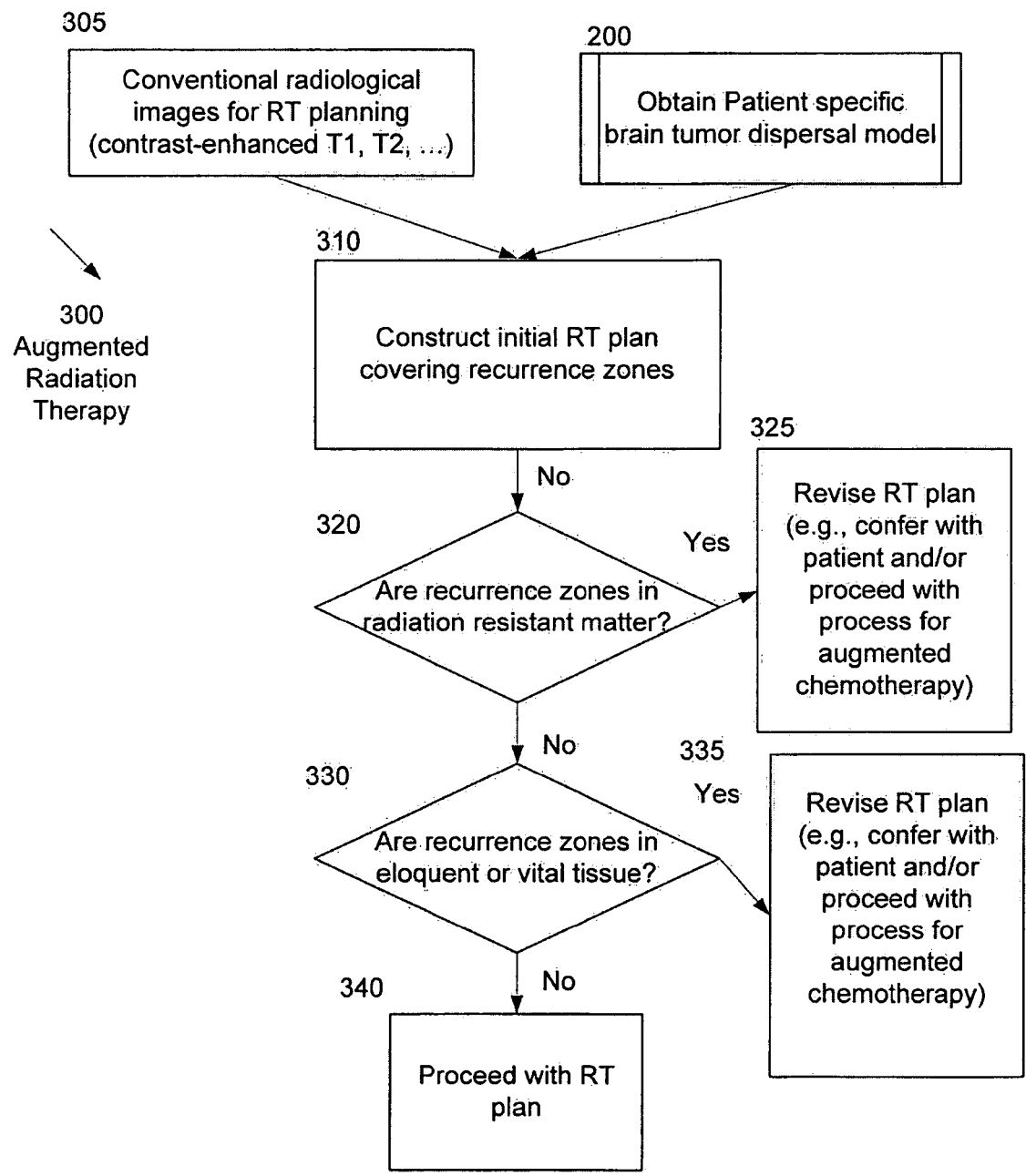

FIG. 3 illustrates how a radiation therapist can utilize the methods and systems described herein for brain tumors, according to one embodiment of the invention. An overlay of high risk recurrence zones is provided from the tumor dispersal model (200 which is the output of FIG. 2) with the radiation therapy (RT) map (305). Those skilled in the art can realize several possible displays of risk of recurrence based on the calculations of the model, including color coding, or contour maps. The radiation therapist or physician then can make decisions based on the new information available to her. Some of the processes that the physician would go through are indicated in 310-340. Current radiation therapy (RT) practice surrounds the contrast-enhancing mass in a Gd-labeled MR acquisition with a margin of 1-2 cm., according to physician judgment. This "ellipsoidal" region can be the target for RT treatment. In one embodiment, information would be presented to the physician that would display likely zones of recurrence of brain cancer from migration of the primary cancer cells, as already described in conjunction with FIG. 2. This is presented to the physician in a clinically useful two- or three-dimensional display (310). Further evaluation of these likely zones of recurrence will often be called for. Thus, depending on the status of the patient, the likely prognosis after treatment, or without it, decisions can be made regarding whether to irradiate regions which may seriously impact the quality of life of the patient (330) or whether to attempt to treat white matter regions which are known to be radiation resistant, or to defer these to surgery or chemotherapy (320). Based on this further information and evaluation, a RT plan for the patient may be constructed (325, 335). The RT plan may then proceed (340).

Figure 4:
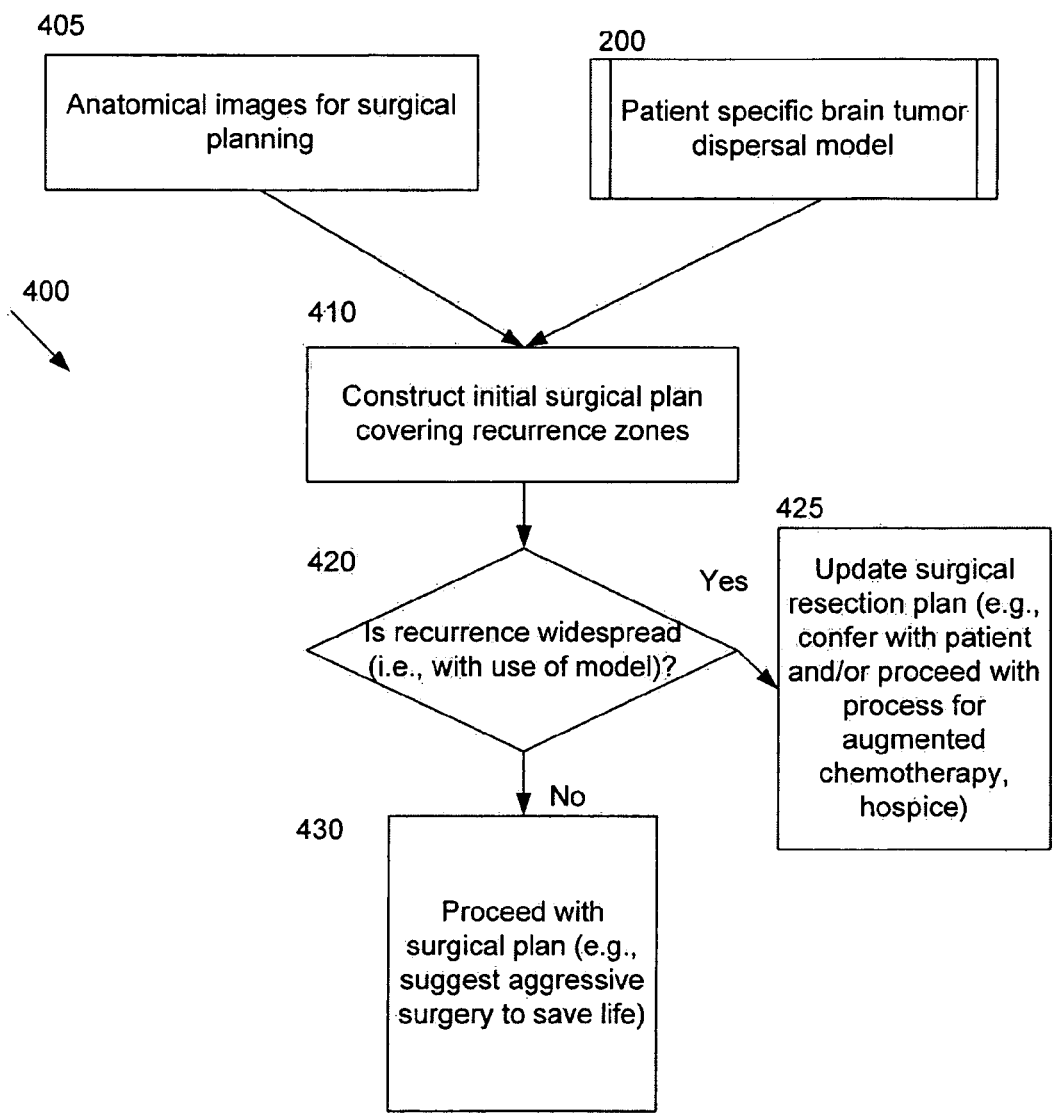

FIG. 4 illustrates a process similar to FIG. 3, which can be utilized by a surgeon as part of the process of surgical resection of tumors. The overlay (410) of zones for high risk of tumor recurrence (200) with the currently available surgical plan (405) can be evaluated by the surgeon to make decisions, as mentioned in the description of FIG. 1A. 410-430 are illustrative of some example decision processes the surgeon may undergo. Current surgical practice can be rather uniform in its approach to treating patients. For example, since malignant glioblastomas are often fatal, surgery can be generally prescribed if the tumor region is in an area with successful surgery rates. However, chemotherapy can be used instead to allow the patient to proceed with their remaining life (which sometimes is only weeks or months) without having the risk of a much altered quality of life. Thus, in one embodiment, a physician can assess differences amongst such cases. As discussed in the text above, the physician can begin with a risk assessment for cancer migration based on the invention (410). One case may well involve a very low risk of cancer spreading throughout the brain and beyond, in which aggressive surgery may be decided upon (430). Another may indicate that the disease has sptead very considerably, in which case other avenues may be pursued (420, 425).

Figure 5:
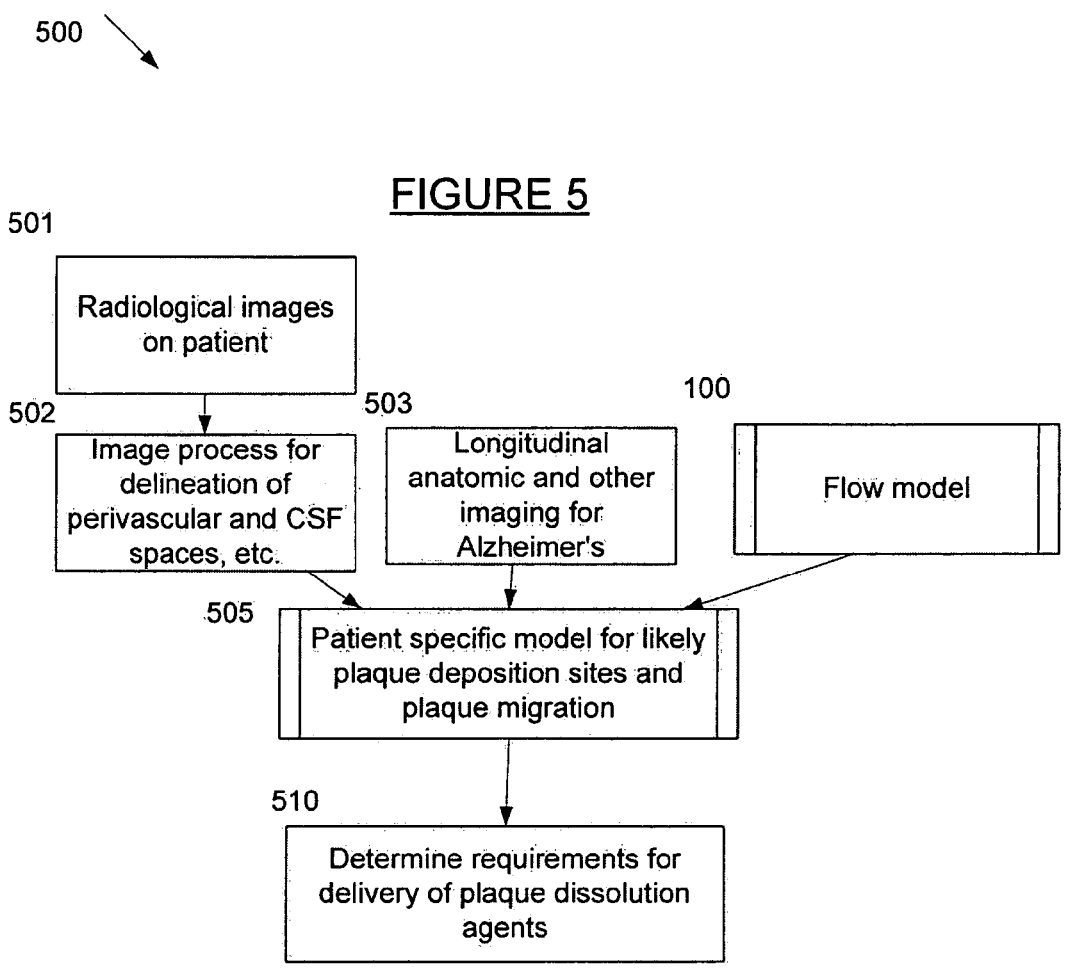

FIG. 5 illustrates a model- and patient image- and data-based map of pathways of deposition of plaque in Alzheimer's, according to one embodiment. In 501, radiological images of the patient are obtained. A careful delineation of perivascular (and/or the Virchow-Robin spaces) is obtained in 502. Those skilled in the art will realize this is obtainable from arterial imaging such as angiography, both in CT and MR modalities, arterial spin labeling (which does not require the invasive injection of a contrast agent), or other methods. These will provide, in combination with delineation of the sulcal grooves and the regions occupied by CSF (the ventricles, and in the sub-arachnoid space), a detailed map of the low pressure intracranial regions. Based on what is known of the etiology of the disease and state of the art imaging on patients, the primary cortical regions of formation of plaque (503) will then be input into the flow model (1100) to provide the most likely pathways for deposition of the plaque. Since the production is cortical, and the CSF spaces closest are often the perivascular, these will provide the more likely regions toward which the plaque will migrate (rather than the deeper ventricular regions). This model (505) will then be presented to the neurologist or physician to determine treatment and prognosis (510).

Figure 6:
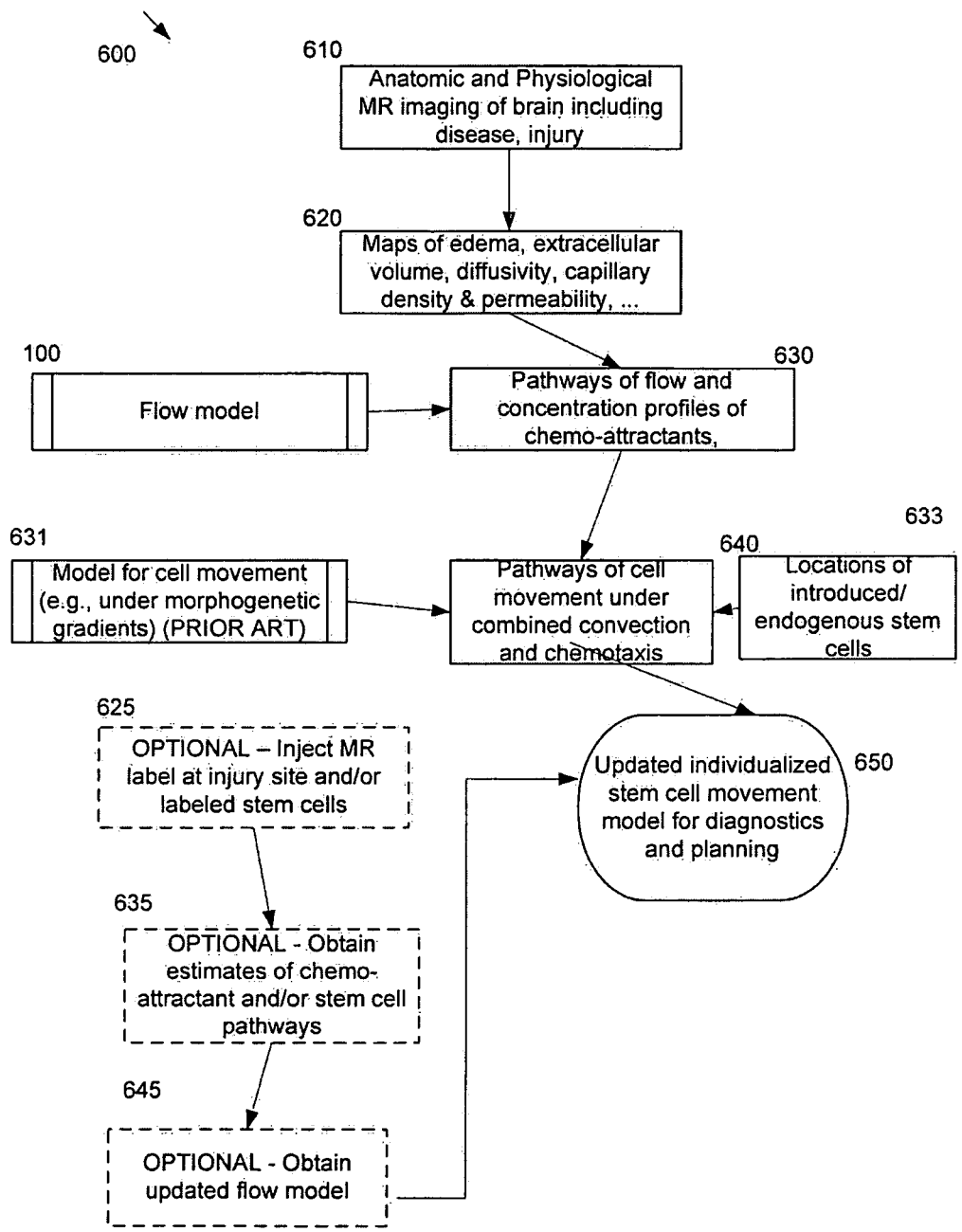

FIG. 6 illustrates a bulk flow model as an inventive component of a model for stem cell migration, both introduced and endogenous, in the presence of injury or disease, according to one embodiment. In injury, there is significant edema and a consequent increase in extracellular volume, as discussed above. This insight removes an obstacle to the understanding of the observed stem cell migration to sites of injury. Under normal circumstances, morphogens do not move more than several cell diameters. A rough order of magnitude estimate can be arrived at from dimensional analysis alone, since the distance scale would be set, absent other factors, by the diffusion coefficient D of the morphogen, and its half-life $\tau$. Then the distance scale one can arrive at would be $L \sim \sqrt{D\tau}$. Assuming, generously, $D \sim 10^{-6}$ cm$^2$/sec and $\tau \sim 10^4$ sec, $L \sim 1$ mm. This is hardly enough to account for migration of cells across hemispheres. Thus, the more efficient process of bulk flow as described above can transport such cytokines over large enough distances to be sensed by remote stem cells. The movement of the stem cells can then be estimated by computed concentrations of the cytokines.

Returning to our description of FIG. 6, imaging (610) such as described for FIG. 1 can provide a detailed map of extracellular volumes (620). The injury is then the source of chemo-attractants and cytokines (such as the stem cell factor (SCF)), and the flow model (100) provides a relative concentration map (in time and space) of such cytokines which are the direction cues for stem cell migration (630). This model can be augmented by diffusive transport and metabolic degradation (these strongly affect the detailed concentration profiles, but have far less impact on the convective wavefronts or pathways populated by the chemo-attractants). The known locations of the introduced or endogenous cells in the brain can also be input (633). Cell movement can also be input (631). In 640, the model can then be a diffusive-convective model which accounts for what is called "chemotaxis" of the cells, which drives them toward the injury source, and the retardation of this migration due to the bulk fluid flow, which, of course proceeds in the opposite direction, being the primary pathway for the dissemination of the chemo-attractants. Such an updated pathways map for stem cell movement (650) has many uses in science and medicine. The field of brain cancer stem cells is in its infancy. These are known, at least in patients with brain tumors, to have residence sites in the sub-ventricular zone, in the dentate gyrus of the hippocampus, and in certain regions of sub-cortical white matter. It will be apparent to any skilled in the art that if knowledge develops of any chemo-attractants for such cells, that the bulk flow and other dissemination of such cytokines can be used to predict likely patterns of spread of brain cancer stem cells.

Injection of an MR label at the injury site and/or labeled stem cells (625), estimates of chemo-attractant and/or stem cell pathways (635), and updated flow model(s) (645) can provide a method and apparatus by which these pathways are experimentally obtained. This alternative route, being invasive, can be exploited more easily in animals, but in any case can also be used in conjunction with the pathways of cell movement model (650) to provide continual refinements and updates.

Figure 7:
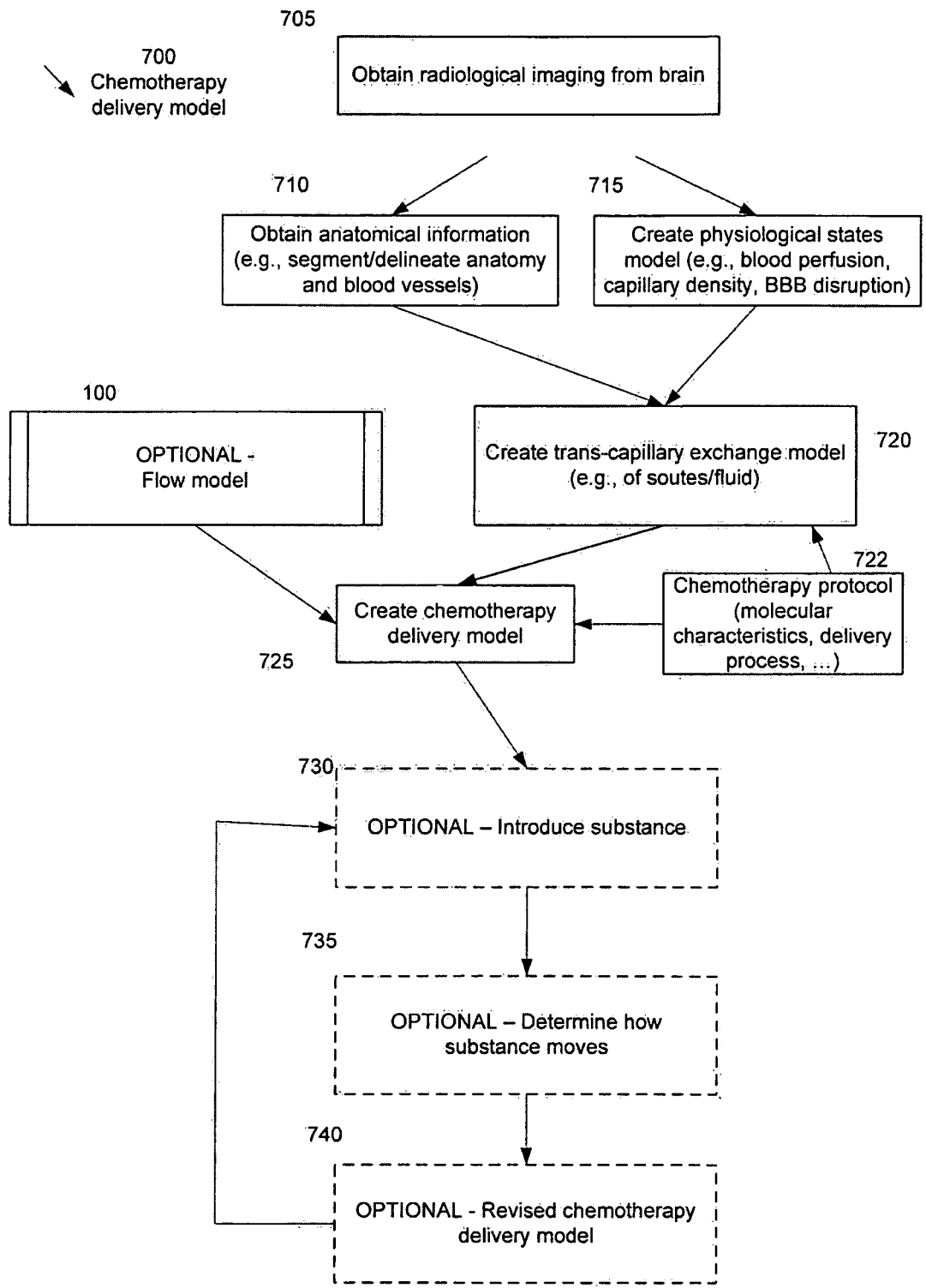

FIG. 7 illustrates a chemotherapy delivery model 700, according to one embodiment. In the previous figures, we describe bulk endogenous flow and convective transport of particulate matter due to such flow. FIG. 7 provides estimates of the distribution within brain parenchyma of systemically introduced particles. FIG. 6 explored endogenous flow. This allowed us estimates of the distribution of particles residing in the brain parenchyma, be they endogenous or introduced for therapeutic or diagnostic reasons. As in FIG. 6, one or more radiological images are obtained. For systemically introduced particles, we need to estimate rates of ingress into, and egress across the blood vessels from, brain parenchyma. Thus, a map of key anatomical characteristics of the blood supply (710) is utilized including the density of the blood vessels and their permeability to molecules introduced in a standard way in perfusion imaging. These can include both MR markers (such as Gd-DTPA) or CT markers. Those skilled in the art can supply a variety of other available methods. The model then employs known scaling estimates, or in-silico measurements to infer the permeabilities and residence times for water soluble proteins of the desired molecular weight. The use of dynamic contrast enhanced imaging (DCE) to construct the parameters relevant to transcapillary exchange have been described above in the section pertaining to DCE and are captured in 715. If the chemotherapeutic molecule is instead lipid-soluble, similar derived estimates from the body of biological research or measurements on available testbeds can be used. However, in this case, scaling from in-vivo measurement from Gd-DTPA are not relevant, since lipid-soluble molecules actively diffuse through the lipid bilayer of the cells constituting the BBB, unlike the water soluble ones to which the BBB is a semi-permeable membrane with barriers alternating with water channels. In either case, based on such estimates, we construct a transcapillary exchange model (720). This, with information about the chemotherapy protocol (722), provides a source term for the entry and the rate of entry of the chemotherapeutic molecule into the parenchyma. The flow model (100) then allows us to create a chemotherapy delivery model (712) and estimate the chemotherapeutic profile and residence time in brain parenchyma. An alternative path would be to observe selected points in the brain for the concentration of the molecule by micro dialysis or other means. A neural network or other statistical estimator can then be used to predict the distribution profile over the entire parenchyma. Its accuracy will depend on the number and distribution of the micro dialysis probes, and of the amount of a priori information, such as the model just described, that is available to the statistical estimator. In 730, 735, and 470, we illustrate another embodiment that can work synergistically with the model construction mentioned above. With the introduction of a substance (730), (such as microdialysis probes, as mentioned), we can follow the concentration of the introduced chemotherapeutic agent (735) in brain parenchyma. The results of these measurements can, in a loop familiar from optimal control theory, be made to influence parameters of the model for a better fit to the data (740). We now describe one theoretical construction of a chemotherapy delivery model.

Chemotherapy Model Mathematical Equations.

For the chemotherapy delivery model, we begin with writing down the equations describing the concentration n(x, t) of the chemotherapeutic molecules. (Usually we suppress the space and time arguments). This is completely analogous to the equations for the albumin and the tracer above $$\frac{\partial n}{\partial t} = -\nabla \cdot (vn) + \nabla \cdot (D_n \nabla n) + q_n - k_d n \qquad \text{(Equation 21)}$$

Note that v is the bulk flow velocity, n are the concentrations, $D_n$ is the diffusion tensor of chemotherapeudic molecule, $k_d$ is the coefficient rate of degradation, and $q_n$ is the interstitial production rate. Thus, the terms on the right hand side represent, from left to right, the convective transport in the interstitium, the diffusive transport therein, the transcapillary transport, and finally the irreversible degradation, metabolism, etc., in the parenchyma. Obviously, we have linearized the last term. We repeat the equations for transcapillary transport $$q_n = \frac{PS_n}{V}(n_v - n) + q(1 - R_n)n_v \qquad \text{(Equations 22, 23)}$$
$$\phi_v \frac{dn_v}{dt} = F(n_A - n_v) - \frac{PS_n}{V}(n_v - n)$$

The chemotherapy molecule-specific parameters are now labeled by the subscript n. Note that $n_v$ is the concentration in the blood vessels, $n_A$ is the arterial input function, $$\frac{PS_n}{V}$$

is the permeability area production for the unit tissue volume, F is the regional cerebral blood flow, and $\phi_v$ is the volume fraction of tissue occupied by blood vessels. In the first of the equations just above, the flow rate per unit volume of tissue has the usual terms due to concentration-driven transport, and convective flow across the capillary walls. We recall that, strictly speaking, $R_n$ should not be labeled an osmotic reflection coefficient, but rather a solvent drag or ultrafiltration coefficient. However, it does not appear in other equations so there is no risk of confusion here. The second equation is similar to that used in DCE (chemotherapy is a very similar process after all). The equation for q, the transcapillary transport of water, can be assumed to be entirely unaffected by the chemotherapeutic molecule so that the osmotic reflection coefficient of the serum albumin proteins alone will enter into it.

We have already discussed the estimation, of the bulk flow velocity v, the cerebral blood flow F, and the plasma filtration rate q above, so we restrict our attention here to methods of estimation of the remaining parameters. These are $$\frac{PS_n}{V},$$

$n_A$, and $R_n$. (We assume that degradation rates are available from pharmacokinetic sources. One example use of the model will be in determining effective coverage of the chemotherapeutic molecule, in which case the long term distribution of an unmetabilized molecule is not of much interest. Thus, the solution for short times with the degradation rate set to zero is of considerable practical interest.) The permeability and the reflection coefficients are sensitive to the ultrastructure of the capillaries, and their variation is important in understanding the effects of the blood brain barrier disruption can be determined by known scalings from the values determined for the tracer molecule. Selection of tracers of similar molecular weight, size, and solubility in water/oil to the chemotherapeutic molecule is to be preferred. However, the literature provides scaling relations for molecules of different size: permeability of globular Water soluble molecules tends to be proportional to $1/\sqrt{MW}$, where MW is the molecular weight, until a certain size, and for a fixed oil/water partition coefficient, and more sophisticated relations and data are available. $n_A$ is determined from the injection protocol.

Figure 13:
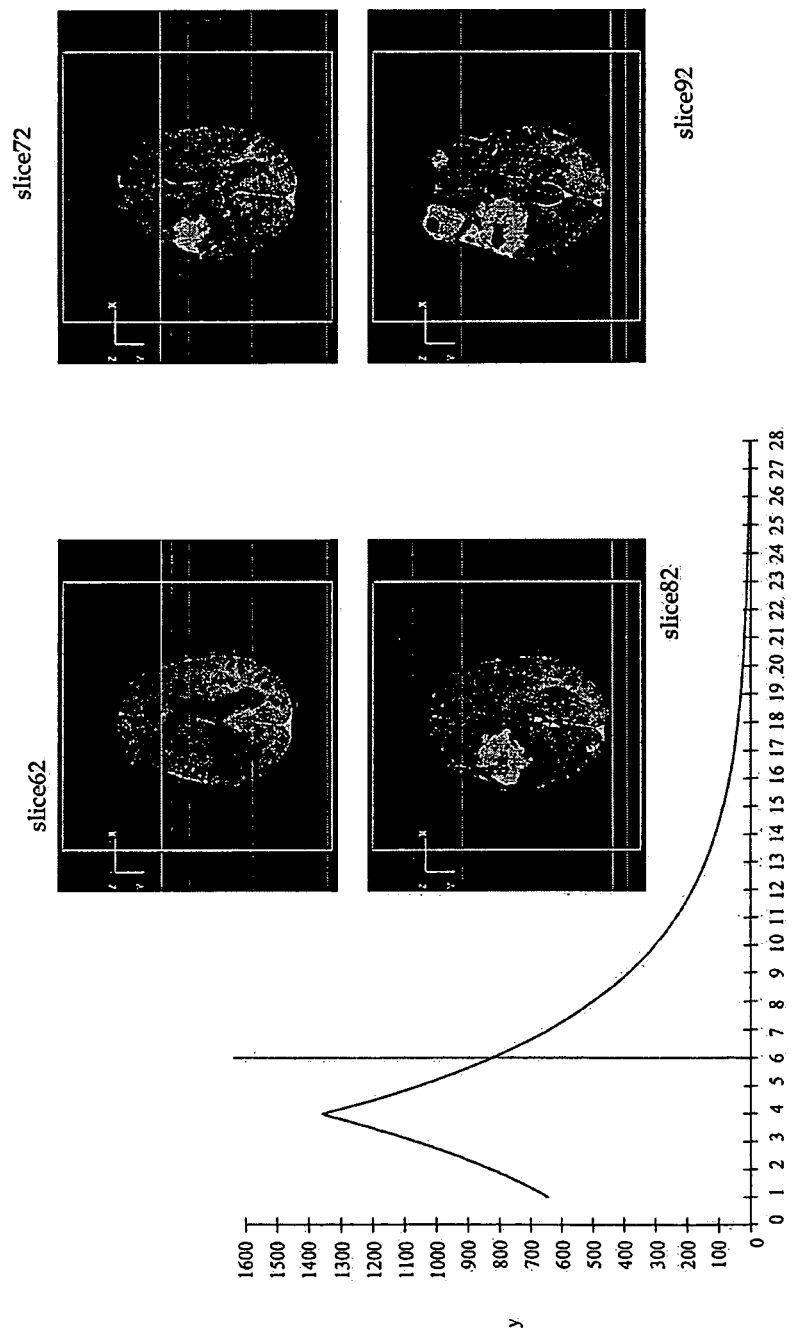
FIG. 13-14 illustrate screen shots that can be used in the system and method, according to several embodiments.

FIG. 13 illustrates an example of a chemotherapy model, according to one embodiment. shown for ease of display in two dimensions (although three dimensions can also be displayed), the chemotherapy model can exhibit a color coded display of the concentration of a chemotherapeutic molecule in selected two dimensional planes. FIG. 13 illustrates pictures of axial slices positioned at different levels along a vertical axis. The color code (white is hot or high, and the cooler colors are low intensities) shows how much of a drug there is at a given time. On the left of FIG. 13 is a graph that shows the corresponding time (in hours, on the abscissa of the graph) as well as the concentration of the drug in the bloodstream. Illustrations such as those showed in FIG. 13 can help in devising chemotherapeutic plans for a patient, and the methodology described herein can take into account the physiological state of the patient such as the status of the blood brain barrier. Different time points are shown in the different images.

Figure 14:
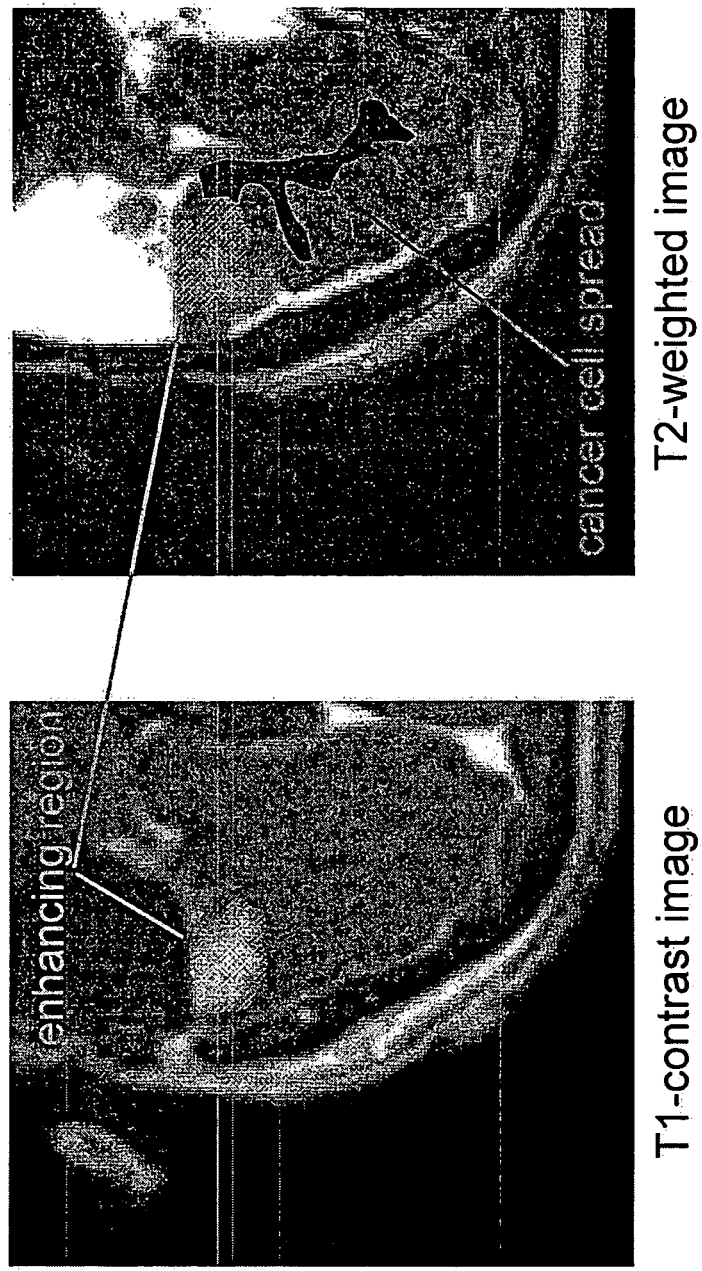

FIG. 14 shows an example of a migration illustration, according to one embodiment. The high risk zones for cancer recurrence are displayed as an overlay on a radiological image (the image on the right of FIG. 14). More refined displays, color coded according to the likelihood for recurrence, may also be envisaged. The spread can be filamentous and quite dependent on direction, as shown in FIG. 14.

Figure 8:
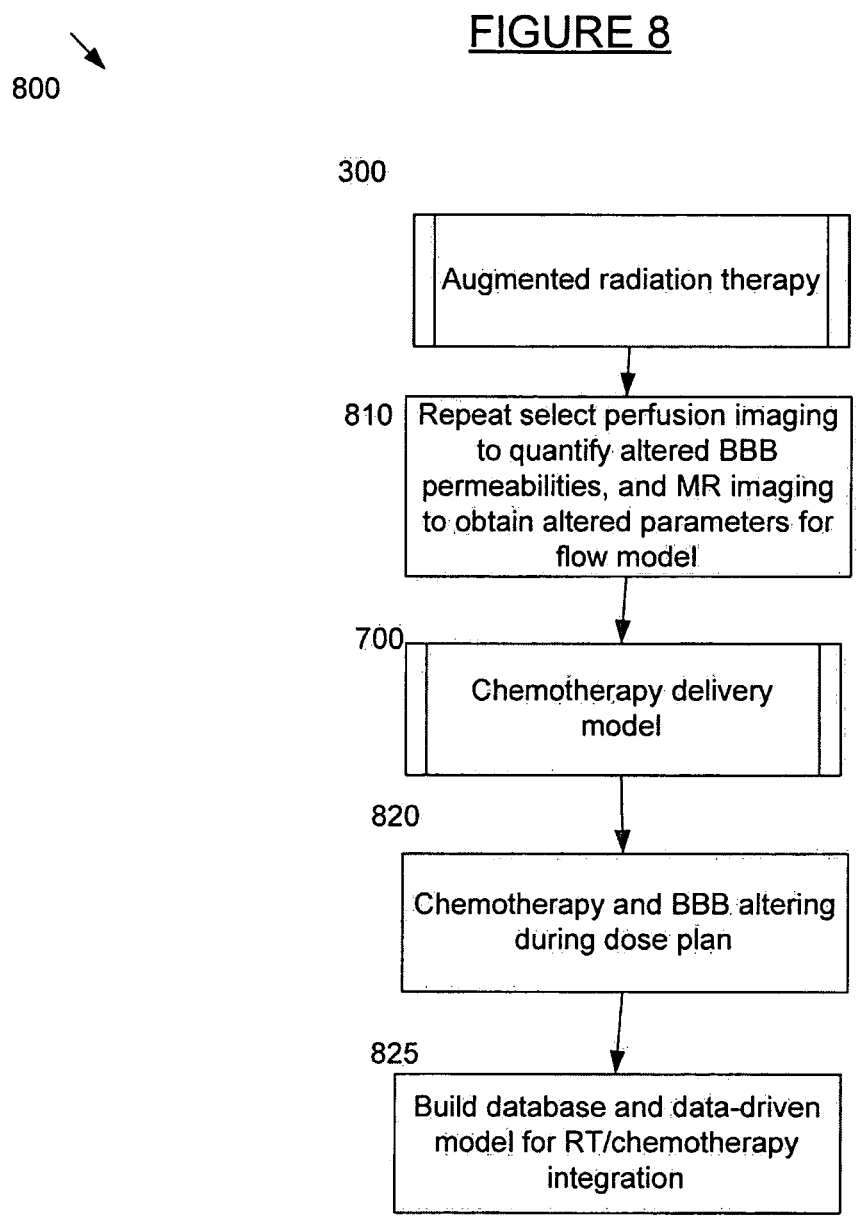

FIG. 8 is a flowchart illustrating RT and chemotherapy integration, according to one embodiment. The BBB permeability is alterable either as a (usually not desired) by-product of treatments such as radiation therapy, or of the deliberate introduction of BBB altering agents. Further systemic introduction of molecules accounting for the newly disrupted BBB can be used along with any consequent ederma (810), by a combination of methods already discussed with respect to FIGS. 1-7. FIG. 8 shows that a particular application of this process and apparatus can be the integration of RT (300) and chemotherapy (700), by taking "advantage" of the increased BBB permeability (820) as a result of RT. In 825, a database and data-driven model can be built for the RT/chemotherapy integration. Another application is to just exercise the chemotherapy delivery model described in FIG. 7, but after the introduction of a BBB altering drug.

Figure 9:
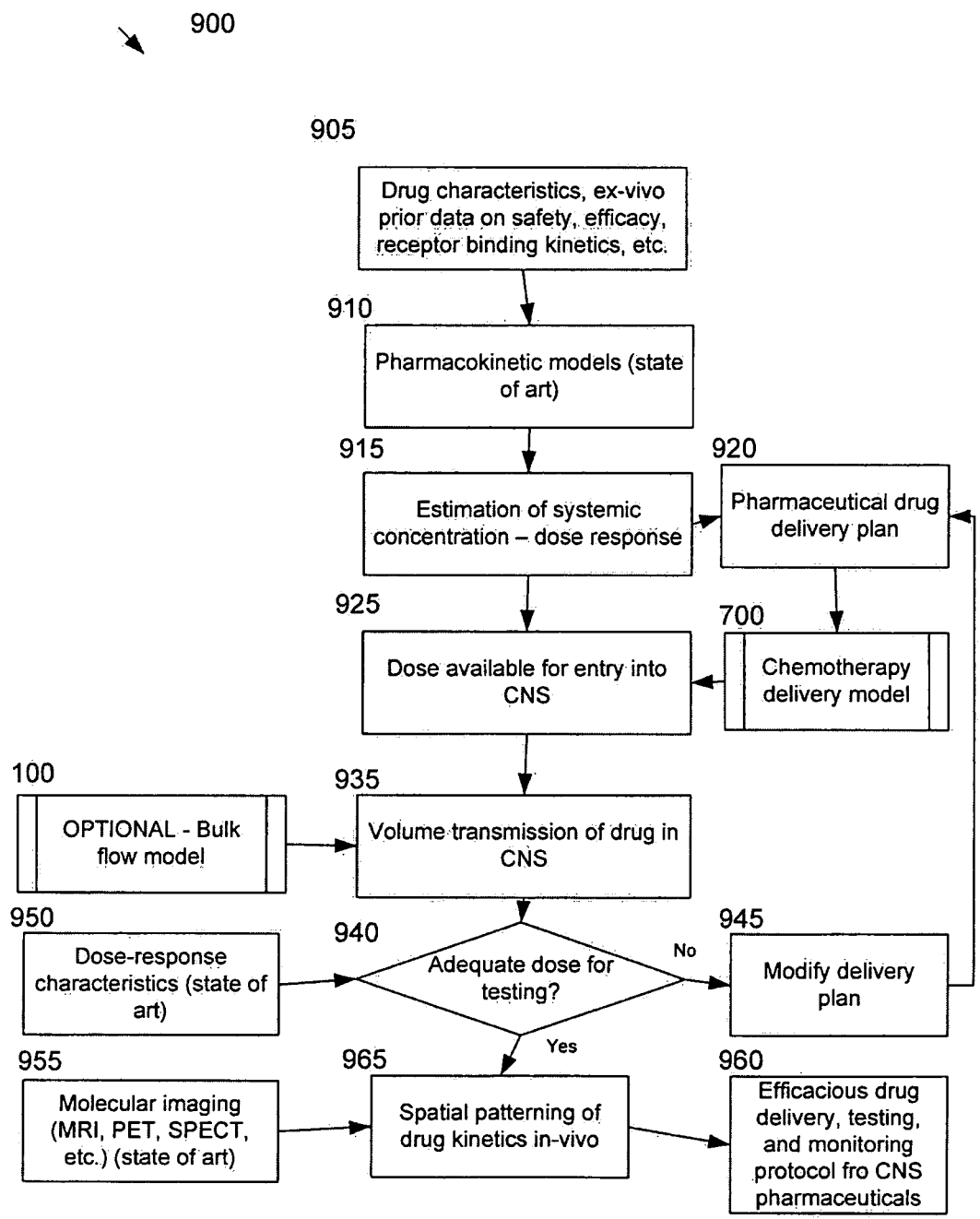

FIG. 9 describes a process in which the system and method can be used as a part of the pharmaceutical drug development process, according to one embodiment. The data collected during early phases of the drug development process (pharmacokinetics and so on, 905) along with the initially estimated desired dose (according to the expected response, 915) is made available as input. As previously described, a profile can be provided of the expected disposition of the agent in brain parenchyma (935). This allows for an iterative refinement of the delivery plan (945) with inputs from the known or estimated dose-response curves (950) which are allowed to be dependent on the disease state of the tissue where desired responses are hoped for.

We note that, in one embodiment, an optimal delivery plan can be generated. We can start with a reasonable first guess for a delivery plan, and based on the desired dose and spatial distribution of the dose, we can alter the delivery parameters within a range. Those skilled in the art will know how to quantify the match of the expected dose to the desired, and thus obtain an "optimal" plan. The variation of the range of delivery parameters can be done at first crudely over large intervals, and then successively refine the intervals to obtain an optimal delivery plan.

We can also integrate advances in molecular imaging as they become available and are desired to be used, to refine the model from the use of current pharmacokinetic data usually obtained in cell cultures, to in-vivo kinetics (955) that is beginning to be available in research laboratories, and will be increasingly available in routine clinical practice. This can, in turn, lead to more refined delivery plans for patient-specific optimization (960). The model used by itself, or in conjunction with these forms of molecular imaging will result in details of the spatial patterns of drugs as they distribute in a living brain (965) which will result in increased utility to the pharmaceutical industry.

Figure 10:
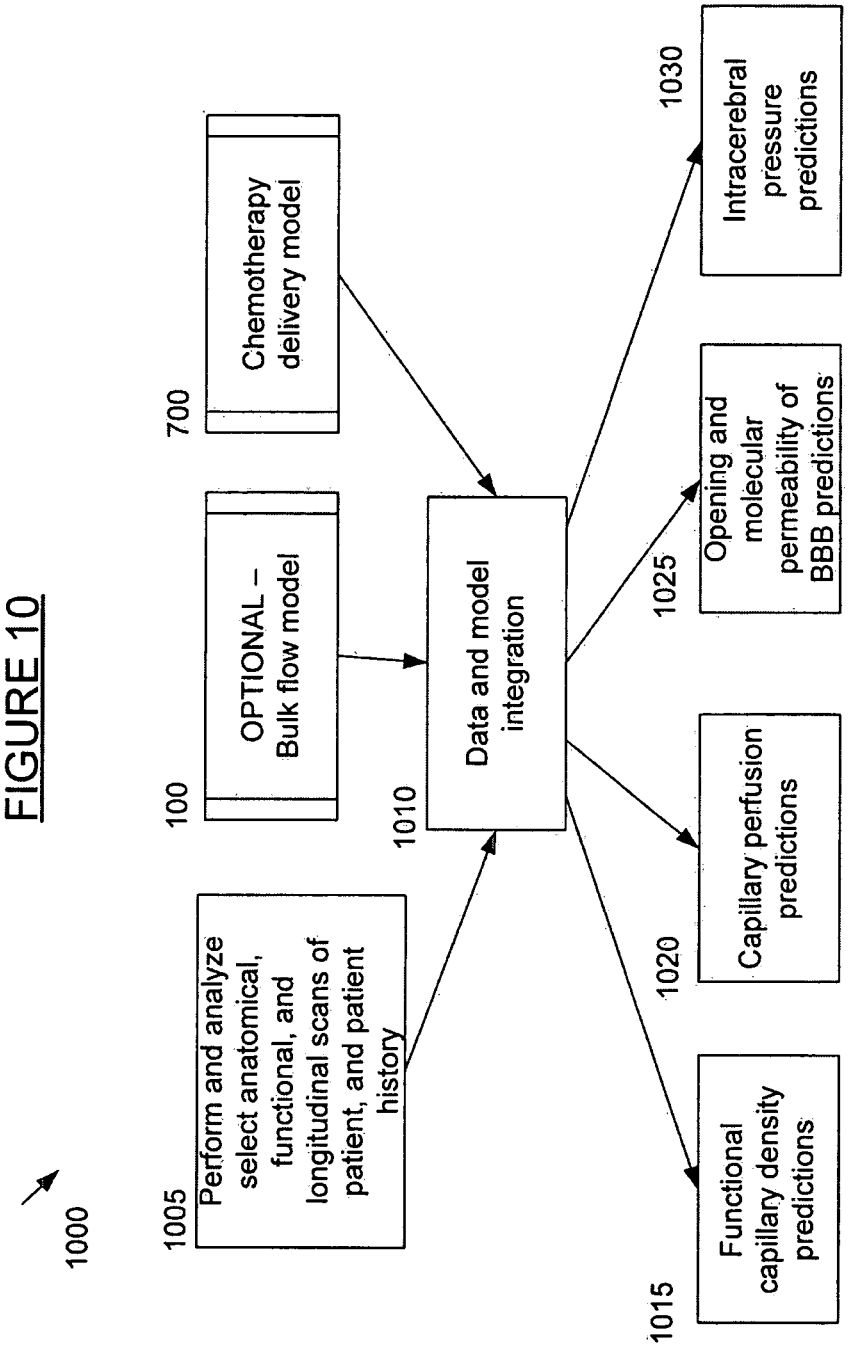

FIG. 10 illustrates example uses of the methods and systems described herein as services to select industries. In particular the continual use of the processes described herein (e.g., flow model 100, chemotherapy model 700) will be enhanced by access to, and performance of, radiological, imaging on a single patient over time, i.e. longitudinally (1005). These can all be combined into an integrated model (1010). This integrated model can be used in many circumstances. For example, an in-vivo estimate of intracerebral pressure variations from imaging (1030) could be of utility as software module in existing scanners and thus of application interest to radiological imaging suppliers. Research and other hospitals could also be interested in some of these components apart from their integrated use in patient care as described in the previous figures. We have described in detail the development and use of a chemotherapy model in the simulation of chemotherapy delivery. It can be envisaged however, that outputs of such a model, such as the functional capillary density, may be used for diagnostic purposes in brain cancer. Such an application could be used in functional capillary density predictions (1015). Similarly, diagnostic and other applications can be envisaged for quantification of blood-brain barrier disruption (1025) or cerebral blood flow (1020). Such applications can also be provided, with methods of display that enhance the clinical utility of the numerical estimates (see below).

User Interface

In one embodiment, a method and system are provided for numerical modeling of the motion of materials (e.g., endogenous and/or therapeutic) in the setting of the human brain as has been detailed above. Extending the usage of microscale and nanoscale to all the metric prefixes, anatomy emphasizes the centiscale and deciscale: This range is referred to as the anatomical scale. Anatomy represents a distinct kind of understanding, with a strong emphasis on characterizing whole tissues by their geometrical and functional relation to their surroundings and the rest of the body. In one embodiment, the microscopic processes of transport are addressed, from molecules to migrating cells, with an emphasis on the role of bulk endogenous flow, particularly when there is injury and consequent expansion of the extracellular spaces. The model can account for the influence of porosity, tortuosity, and other microscale features while drawing on milliscale data from 3D scanning (e.g., CT for anatomical detail, MR for concentration and diffusion tensor estimation, edema) to construct and solve appropriate partial differential equations (PDEs). Scalar or tensor values can be provided, distributed in space with features such as a point of maximum concentration, but without sharp boundaries. In one embodiment, these models can predict and improve the targeting of drugs across the blood-brain barrier, and predict the spread of cellular material within the brain in addition, in one embodiment, these models can be clearly displayed and used. Thus, a clinician can select a protocol in a series of cases, predict the outcome, and compare it with outcomes clinically predicted for other options. If, in a substantial proportion of cases, a better outcome appears available than with the clinician's choice, and the prediction of this better outcome has a substantial degree of confidence, then the potential for clinical improvement exists.

It should be noted that the clinicians' predictions can be improved if they can theorize as a researcher. A researcher can predict outcomes for other protocols chosen with complete freedom, allowing multiple attempts and inspection of details via close familiarity with the workings of the model. For example, a researcher could determine that there is not much migration to the lesion, but what migration there is appears to be via a certain edematous region, so the researcher could theoretically move the injection site to other regions, which is upstream of the edema in CSF circulation. Clinical utility is thus assisted by an interface which makes such exploration fast and effective.

In one embodiment, data from PDEs is extracted to create a network representation of the brain's transport properties for the material considered, summarizing and approximating them by a 3D structure of curves joining nodes. This assists in multiple purposes: 'lumped' approximate computation, clear visualization, effective interaction and planning, an explicit relation with anatomical concepts, etc. The curves and nodes of the model make anatomical sense and can allow automated anatomical labeling.

This comprehensible and anatomically meaningful representation of vital processes in the brain, from the perfusion of a drug to the migration of stem cells and metastasizing tumor cells, can create new anatomical understanding by empowering thought about the interaction between structure and process dynamics. The transport network representation acts as a mental and computational bridge between anatomy, on the scale of the brain in the large, and detailed transport biophysics modeled on the nano- and microscales and computed on the milliscale. Both as a descriptor of transport in the 'general brain' and in patient-specific instances, where the representation is built afresh from patient data, it can lead to new levels of understanding of the dynamic relation among the brain and its parts.

Creating a Detailed Display of Brain Tissue

High description of tissue gives not merely its shape and position, but its function, and clinically all of these must be patient-specific. We here address the extraction of structured information at a high level, arising from work with data gathered and handled on a milliscale grid, and modeled by equations structured by our knowledge of processes on the micro- and nanoscale, such as flow through a medium with tortuous pores, and cellular take-up of Materials.

For clinical use, software exploiting our algorithms can display results at the centiscale and even the brain-spanning deciscale. The anisotropy of flow in the brain gives rise to pseudochannels described in more detail below, defined as curves along which maximal effective transport (a maximum eigenvalue cmax of the relevant tensor) is greater than along all neighboring curves. Such a curve is most channel-like when cmax most exceeds the other eigenvalues, but the definition generically gives smooth curves wherever the larger two eigenvalues are distinct. (Equality combined with the maximality conditions gives branch points, and hence nodes in the network.) This can thus support a powerfully annotated network view when choosing injection points, and a basis for patient-specific network models.

The channel extraction logic can directly map mechanical transport properties; but nerve bundle geometry, with long extracellular spaces between closely packed cylindrical axons, can show the major neural pathways as pseudochannels. We thus can identify major nerves, using anatomical referents to identify which nerve is which and thus to present them as named top-level structures connecting with the large body of knowledge that exists at this level rather than at finer scales. In particular, this can allow software to warn when a surgical plan (pre- or intra-operative) comes dangerously close to one of these key structures.

Since so many of the brain's processes consist of or involve signaling, at a range of speeds from the nerve impulse to the migration of stem cells and metastasizing tumor cells, we are thus providing the foundations for a systematic functional map, firmly rooted in individual rather than average or idealized brains, and for software that will use it in practical planning assistance to the clinician (e.g., surgeon).

In one embodiment, a systematic digital embodiment of the relation between the large-scale structure of the brain is provided, including many functional properties, and the scale at which it is practical to compute material transport, which in turn involves cellular and membrane processes best understood on the micro- and nanoscales.

In one embodiment, a system and method are provided for creating a representation of (modeled) transport properties of the brain which is transparent and usable to the clinician. Density fields with few discontinuities are both hard to display clearly, and hard to think about. The clinician knows far more of the patient's brain anatomy, physiology, localization of function, eloquent regions, sensitivity to invasive trauma, and so on than can be embedded in current software. Our schema extracts from the field data of the PDEs in the model a network representation of the brain's transport properties for the material considered, summarizing and approximating them by a 3D structure of curves joining nodes. This will be valuable for multiple purposes: 'lumped' approximate computation, clear visualization, effective interaction and planning, and an explicit relation with anatomical concepts. The curves and nodes make anatomical sense and in many cases allow automated anatomical labeling. The curves can be constructed for the transport of any material of interest, from small molecules to cells. In some embodiments, we expect (anatomically) a great deal of commonality, but not identity, between the networks constructed for different materials. Any curve that appears in all or most of them (in the sense that in each network a curve can be chosen that is a good approximation of a corresponding curve chosen in another network), will usually correlate with an important anatomical structure.

Figure 11:
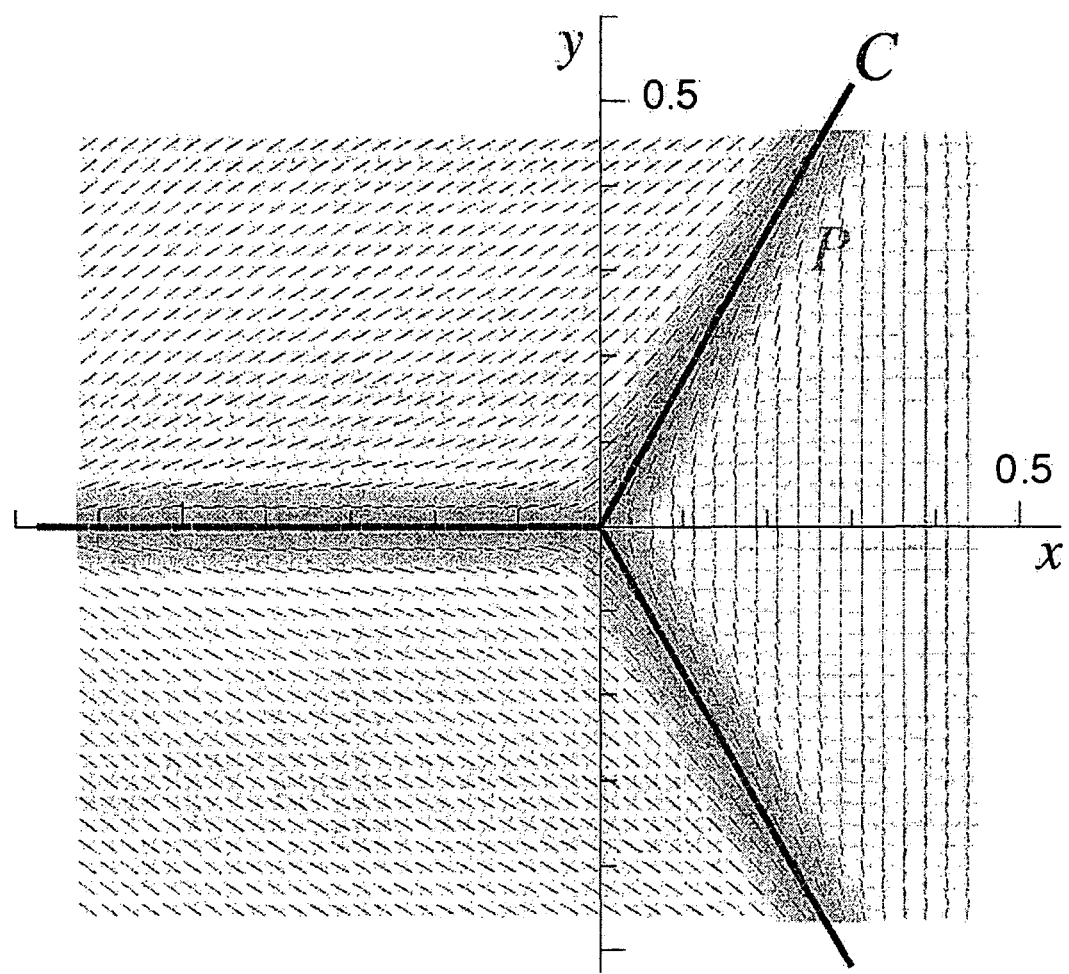
FIGS. 11-12 illustrate behaviors that affect a user interface utilized for providing information for treating brain disease, according to several embodiments.

The idea of flow along a curve, even a curve in three dimensions is of course a simplification. Real materials move as evolving concentrations, as reflected in our equations. (Even at the particle level, shared paths exist only statistically.) However material transport in the brain has phenomenological paths of some importance. For example, there is the pseudochannel, any narrow region for which transport is easier along it than either across it or along nearby curves in the same direction. A pseudochannel tends to capture a large part of any flow that is active in the volume it lies, and is a feature of the three-dimensional landscape. We can quantify this idea by defining the core of a pseudochannel as a curve along which the greatest effective diffusion coefficient cmax (an eigenvalue of the EDC tensor) is greater than at any nearby point in the directions belonging to the lesser eigenvalues. This may be illustrated in the plane by the tensor field (which is in fact the Hessian of $[(1+r\cos(3\theta))r2/2+r4]$, though not every symmetric 2 tensor arises from a scalar field). FIG. 11 shows strong eigen directions in black, weak ones in gray. The core C consists of points where the large eigenvalue cmax is greater than at 'sideways' neighboring points. (In general cmax also varies in its own direction, and requiring maximality there would give us isolated points.) At points where the eigenvalues—in 3D, the two greatest eigenvalues—are equal, the curve branches. FIG. 11 includes a generic example. The types of branching may be classified by means analogous to those in modern mathematics of the differential geometry of curves and surfaces, and the corresponding use of higher expansion coefficients leads to effective numerical siting of particular instances. Branch points give rise to nodes in the network of core curves.

In constructing a network we will use a combination of fine-scale and large-scale criteria to prune off clutter. A short side branch that goes nowhere, and has cmax values that are only gently greater than the other eigenvalues at each point of this side branch, or are unsharply maximal across it, will be discarded. Even a numerically weak segment that affects the overall connectivity of the network will be retained.

Strictly, the definitions here involve tensor fields and differentiation defined on an infinitely divisible continuum with no characteristic directions of its own (as distinct from anisotropy of the fields), while our computations are on a discrete rectangular grid at the milliscale.

For a thin channel the decrease through neighboring curves is rapid, so that transport will be concentrated in a pseudochannel P around C. This does not have sharp borders, but we approximate an effective thickness from the size of quadratic coefficients in the Taylor expansion of cmax across C. Combined with the directional coefficient cmax itself, this gives an approximate transport coefficient along the pseudochannel at each point on C, which can be integrated by 'in series' logic to give a single lumped channel capacity number for each curve segment between nodes. This allows rapid, approximate calculations of total transport through the brain, on the anatomical scale: We can tune the channel capacity estimator and the channel transport dynamical equations for the best agreement we can reach with the milliscale PDE solutions that give more accurate results. They can thus support an overview navigation system through the PDE model. We can display a network of 3D channels color-coded for cmax value, thickness and approximate capacity. Superposed on translucent brain anatomy, this provides a powerfully and interactively annotated view when choosing injection location, pressure parameters, etc. Expected network transport can be computed and updated in real time as the user moves a choice, and the channel view will give strong cues as to what direction to move for improved results (both in increasing delivery to a target, and in reducing it in tissues vulnerable to side effects). Choices can be checked and fine tuned by invoking the milliscale model, but the interactive process of using the simulation can be greatly strengthened by comprehensible display of transport behavior at the anatomical scale.

Figure 12:
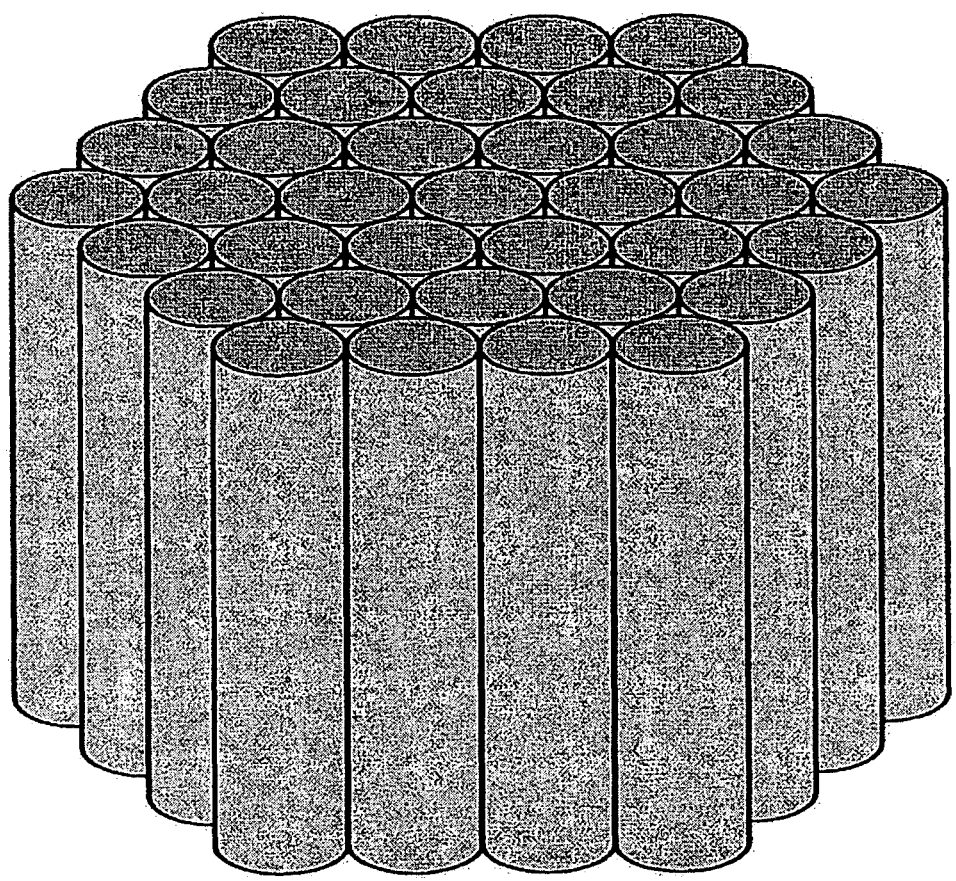

In one embodiment, the network thus constructed from milliscale transport data is not merely visualizable on the anatomical scale, but meaningful at this scale. The anisotropies of transport are not anatomically arbitrary, but arise from structure. For example, a major nerve is a closely packed bundle of near-cylindrical axons; away from cell bodies, such assemblies tend to arrange themselves hexagonally, as shown in FIG. 12, so that the extracellular transport medium occupies the long spaces between them. Even with the irregularities of real cell assemblies, averaging gives to the transport coefficient tensor for most materials a largest eigenvalue direction aligned with the bundle. Other anatomical features such as the inner folding of the cortex (as distinct from the outer folds, or sulci, outside the blood-brain barrier), also impact transport properties. A ventricle is visible in various imaging modalities: it acquires transport anisotropy only by forced or natural flow of the cerebrospinal fluid they contain, but where narrow on the scale of averaging used in diffusion tensor scanning, the resulting field is anisotropic. This must be recognized and connected to the ventricle as a distinct class of object in the transport network. We can analyze carefully the relation of all these features in the primary scans on which we build and test our system, first identifying the anatomy involved in each branch of the pseudochannel network, then automating as far as possible the recognition process in new data, for the more reproducible segments and nodes. The resulting anatomically annotated transport map can have a more direct relation to the mental framework of the practicing surgeon or radiologist than a visualization of intensities alone can accomplish. Moreover, as the normal range of transport maps becomes apparent through use with multiple patients, abnormalities may become highly recognizable to the human user. Since transport is a fundamental process in the brain, this could provide an important new diagnostic tool.

For an actual computed or measured transport we can define the streamlet, similarly defined from the flow field and visualizing the flow more clearly than is easily achieved with a density map in 3D. (In a plane an animated map of levels, smoothly color-coded rather than shown by level contours, shows flow very clearly. Visualizing smooth scalar Variations in 3D space is far more difficult.)

In one embodiment, software can be constructed as follows: (1) A numerical definition of pseudochannels can be provided. Numerical algorithms can be built for the identification of maximal-eigenvalue curves, applied to the measured diffusion tensor and to transport-tensor fields constructed numerically using biophysical model equations. (2) A numerical definition of pseudochannel nodes can be provided. Where two eigenvalues are co-maximal relative to those at nearby points, the associated curves generically branch. Such points can be identified numerically and characterize the branching directions. (3) Ventricles can be characterized. Ventricles can be identified from scan data and their transport properties can be quantified. (4) Construction of a 3D pseudochannel network can take place. Ventricles and pseudochannel curves and nodes can be assembled into an object oriented model of a graph embedded in three-dimensional space. (5) A streamlet network can be constructed. Given a specific flow field, derived from experimental data or tracked transport, the above algorithms can be used to create a user-understanding-friendly 'sketch' of it, as a graph analogous to the pseudochannel network. (6) Lumped network dynamics can be optimized. Pseudochannel 'thickness' can be quantified as a measure inverse to how sharply peaked it is relative to neighboring maximal-eigenvalue curves, and a lumped 'channel capacity' can be derived to be associated with transport between the nodes it joins. This characterization and a model of flow dynamics can be tuned along the network, for best agreement with numerical solutions of full partial-differential-equation (PDE) flow in the underlying tensor field from which the network was derived. (7) Network elements can be anatomically identified. Anatomical comparison can be used with patient scan data to identify some pseudochannels and nodes with named brain features such as nerve bundles and portal systems. Algorithms can be created to automate such identification in new patient data. (8) The visual setting of the brain can be displayed in a 3D display. An interface can be created by which a user can see the relation of the network to a translucent volume display of a scanned brain, with channel properties coded by color and geometric thickness: The cognitive value and immediacy of different coding schemes can be explored. Numerical experiments can be enabled with user placement of a bolus of material for transport and display of results from both the network model and the finer-scale PDE model.

CONCLUSION

While various embodiments, of the present invention have been described above, it should be understood that they have been presented by way of example, and not limitation. It will be apparent to persons skilled in the relevant art(s) that various changes in form and detail can be made therein without departing from the spirit and scope of the present invention. In fact, after reading the above description, it will be apparent to one skilled in the relevant art(s) how to implement the invention in alternative embodiments. Thus, the present invention should not be limited by any of the above described exemplary embodiments.

In addition, it should be understood that any figures, screen shots, tables, examples, etc. which highlight the functionality and advantages of the present invention, are presented for example purposes only. The architecture of the present invention is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope of the present invention in any way.

It should be noted that the phrase "comprising . . . a" throughout the claims means "comprising . . . at least one".

Furthermore, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

The invention claimed is:

1. A method for providing planning and dispensation of research and/or treatment for brain disease, comprising:
    generating radiological information in a region of interest in an area of the a brain of an individual using a radiological imaging system, the region of interest comprising a pathological lesion associated with the brain disease and an area outside the pathological lesion;
    constructing, using a computer, a physiological states model which assesses physiological states of the region of interest;
    obtaining, using the computer, locations of sources of interstitial fluid flow, fluid conductivities of paths, and anatomical information in the region of interest using the radiological imaging information;
    computing, using the computer, velocities of the interstitial fluid flow in the region of interest using the physiological states model, the locations of sources of interstitial flow, the fluid conductivities, and the anatomic information, wherein said computing takes into account changes in interstitial fluid flow caused by the pathological lesion;
    creating, using the computer, a model of the area of the brain including the region of interest, wherein said model shows the computed velocities of the interstitial flow and interstitial pressure variations in the interstitial fluid changed due to the pathological lesion, within and outside the lesion in the region of interest; and
    displaying the model for the planning and the dispensation of research and/or treatment for brain disease.

2. The method of claim 1, wherein the anatomical information comprises:
    information regarding major fiber tracts in a brain;
    information regarding a cerebral cortex;
    information regarding blood vessels in the brain;
    information regarding cells in the brain; and/or information regarding cerebral spinal fluid regions in the brain.

3. The method, of claim 1, wherein the physiological states model is constructed utilizing the anatomical information.

4. The method of claim 1, wherein a strength of the sources is determined.

5. The method of claim 1, further comprising:
    injecting a substance which can be imaged into a brain;
    obtaining estimates of velocities of flow and interstitial pressure variations based on movement of an introduced substance in the brain; and
    creating an updated model of the area of the brain outside the pathologic lesion based on the estimates obtained from the introduced substance.

6. The method of claim 5, wherein the injected substance is not injected in brain tissue.

7. The method of claim 5, wherein the injected substance is injected in blood vessels.

8. The method of claim 1, wherein the model of the area of the brain including the region of interest comprises a model of the area of the brain outside the pathological lesion, and wherein the method further comprises:
    analyzing a radiological image for a brain of a particular patient; and
    creating a patient specific flow model utilizing the model of the area of the brain outside the pathological lesion and radiological imaging of the brain of the particular patient.

9. The method of claim 8, further comprising:
    analyzing radiological imaging recurrence data as a disease progresses; and
    creating an updated patient specific flow model utilizing the patient specific flow model and the radiological imaging recurrence data.

10. The method of claim 8, further comprising:
    obtaining a radiation therapy plan;
    determining if the radiation therapy plan covers significant predicted recurrence zones utilizing the patient specific flow model and the radiation therapy plan, and
    if the radiation therapy plan covers significant predicted recurrence zones, proceeding with the radiation therapy plan.

11. The method of claim 10, further comprising:
if the radiation therapy plan does not cover predicted recurrence zones, determining if any recurrence zones are in radiation resistant matter; and
if any recurrence zones are in radiation resistant matter, creating an updated therapy plan which accounts for the recurrence zones in the radiation resistant matter.

12. The method of claim 11, wherein the updated therapy plan includes:
an updated radiation therapy plan;
a surgery plan; and/or
a drug delivery plan.

13. The method of claim 11, further comprising:
if the recurrence zones are not in the radiation resistant matter, determining if any recurrence zones are in vital tissue; and
if any recurrence zones are in vital tissue, creating an updated therapy plan which accounts for the recurrence zones in the vital tissue.

14. The method of claim 13, wherein the updated therapy plan includes:
an updated radiation therapy plan;
a surgery plan; and/or
a drug delivery plan.

15. The method of claim 13, further comprising:
if none of the recurrence zones are in vital tissue, creating an updated radiation therapy plan which expands the recurrence zones and/or augments a planned dose.

16. The method of claim 15, wherein the model of the area of the brain in the region of interest comprises a model of the area of the brain outside the pathological lesion, and wherein the physiological model, an interstitial model, and a model of the area of the brain outside the pathological lesion are made under normal or diseased conditions.

17. The method of claim 16, wherein the diseased conditions comprise a primary brain tumor and/or Alzheimer's disease with deposition of plaque.

18. The method of claim 8, further comprising:
obtaining a surgical resection plan;
determining if the surgical resection plan covers significant predicted recurrence zones utilizing the patient specific flow model and the surgical resection plan; and
if the surgical resection plan covers significant predicted recurrence zones, proceeding with the surgical resection plan.

19. The method of claim 18, further comprising:
if the surgical resection plan does not cover significant predicted recurrence zones, determining if recurrence is widespread, and
if the recurrence is widespread, creating an updated surgical resection plan based on the widespread recurrence.

20. The method of claim 19, further comprising:
if the recurrence is not widespread, creating an updated surgical resection plan including more aggressive surgery.

21. The method of claim 1, wherein the model of the area of the brain including the region of interest comprises a model of the area of the brain outside the pathological lesion, and the method further comprising:
obtaining a cell movement model of a brain;
obtaining a stem cell migration model of the brain utilizing the model of the area of the brain outside the pathological lesion and the cell movement model;
analyzing radiological imaging of the brain of a particular patient; and
creating a patient specific cell migration model of the patient's brain utilizing the model of the area of the brain outside the pathological lesion and the radiological imaging of the brain of the particular patient.

22. The method of claim 1, further comprising:
creating a trans-capillary exchange model which estimates where and how easily chemotherapy molecular material moves in and out of a brain utilizing the physiological states model; and
creating a chemotherapy delivery model utilizing the trans-capillary exchange model.

23. The method of claim 22, further comprising:
injecting a substance which can be imaged into the brain;
obtaining estimates of chemotherapeutic delivery based on the movement of the introduced substance in the brain; and
obtaining an updated chemotherapy delivery model based on the estimates obtained from the introduced substance.

24. The method of claim 23, further comprising:
obtaining a radiation therapy plan;
selecting perfusion imaging to quantify altered blood brain barrier permeabilities;
obtaining a chemotherapy delivery model;
analyzing radiological imaging of the brain of a particular patient; and
creating a patient specific cell migration model of the patient's brain utilizing the radiation therapy plan, the selected perfusion imaging, the chemotherapy delivery model, and the radiological imaging of the brain of the particular patient.

25. The method of claim 22, further comprising:
analyzing radiological imaging of the brain of a particular patient; and
creating predictions regarding functional capillary density, capillary perfusion, disruption of the blood-brain barrier and molecular permeability, and/or intracerebral pressure utilizing the model of the area of the brain outside the pathological lesion, the chemotherapy delivery model, and the radiological imaging of the brain of the particular patient.

26. The method of claim 1, wherein the individual is an animal and/or a human.

27. The method of claim 1, where the radiological imaging information comprises magnetic resonance imaging (MRI), including diffusion-weighted imaging (DWI), diffusion tensor imaging (DTI), dynamic contrast-enhanced imaging (DCE), and/or arterial spin labeling (ASL).

28. The method of claim 27, wherein the ASL is with magnetization transfer imaging (MTI).

29. The method of claim 1, wherein the physiological states model comprises a mathematical model of transport of hydrophilic plasma proteins across the blood vessel.

30. The method of claim 1, wherein the model of the area of the brain including the region of interest comprises a model of the area of the brain outside the pathological lesion, and wherein the model of the area of the brain outside the pathological lesion accounts for:
variations in hydrophilic proteins in an interstitium of a brain of a living patient;
variations in interstitial pressure in the brain of the living patient;
likely sites of recurrence of a primary brain tumor cells;
mapping migration of the primary brain tumor cells;
mapping extracellular fluid pathways in the brain relevant for deposition of amyloid plaque in Alzheimer's disease; or
planning therapy to dissolve the deposited plaque; or
any combination thereof.

31. The method of claim 1, wherein the model of the area of the brain including the region of interest comprises a model of the area of the brain outside the pathological lesion, and wherein the radiological imaging information is specialized to delineate Virchow-Robin spaces and the model of the area of the brain outside the pathological lesion is used to predict likely migration and deposition sites for coagulated proteins manufactured by diseased cortical neurons.

32. The method of claim 1, further comprising:
obtaining drug characteristics of a drug and ex-vivo prior data for the individual;
obtaining pharmacokinetic model utilizing drug characteristics and ex-vivo prior data;
obtaining an estimate of systemic concentration of the drug utilizing a pharmacokinetic model;
transmitting the drug into a central nervous system (CNS);
determining if an adequate dose of the drug was used for testing;
if the dose was adequate for testing, obtain spatial patterning of kinetics of the drug in-vivo; and
obtain efficacious drug delivery, testing, and/or monitoring protocols for CNS pharmaceuticals.

33. The method of claim 32, further comprising:
if the dose was not adequate for testing, modifying the delivery plan by taking into account a pharmaceutical drug delivery plan and a chemotherapy delivery model.

34. The method of claim 1, further comprising obtaining particulate material flow and distribution in the region of interest using the physiological states model.

35. The method of claim 34, wherein particulate material is:
cellular material;
molecular material; and/or
viral material.

36. The method of claim 35, further comprising:
determining likely plaque migration pathways and/or deposition sites utilizing a patient specific flow model; and
determining requirements for delivery of plaque dissolution agents.

37. The method of claim 1, further comprising obtaining the pressure variations in the region of interest using the physiological states model.

38. A system for providing planning and dispensation of research and/or treatment for brain disease, comprising:
a radiological imaging system configured to generate radiological information in a region of interest in an area of a brain of an individual, the region of interest comprising a pathological lesion associated with the brain disease and an area outside the pathological lesion;
a computer having an application stored therein for causing the computer to:
receive the radiological information;
construct a physiological states model which assesses physiological states of the region of interest;
obtain locations of sources of interstitial fluid flow, fluid conductivities of paths, and anatomical information in the region of interest using the radiological imaging information;
compute velocities of the interstitial fluid flow in the region of interest using the physiological states model, the locations of sources of interstitial flow, the fluid conductivities, and the anatomical information, wherein the computing takes into account changes in interstitial fluid flow caused by the pathological lesion; and
create a model of the area of the brain including the region of interest, wherein said model shows the computed velocities of the interstitial flow and interstitial pressure variations in the interstitial fluid changed due to the pathological lesion, within and outside the lesion in the region of interest; and
a display for displaying the model for the planning and the dispensation of research and/or treatment for brain disease.

39. The system of claim 38, wherein the anatomical information comprises:
information regarding major fiber tracts in a brain;
information regarding a cerebral cortex;
information regarding blood vessels in the brain;
information regarding cells in the brain; and/or information regarding cerebral spinal fluid regions in the brain.

40. The system of claim 38, wherein the physiological states model is constructed utilizing the anatomical information.

41. The system of claim 38, wherein a strength of the sources is determined.

42. The system of claim 38, wherein the computer is further configured to:
obtain estimates of velocities of flow and interstitial pressure variations based on movement of an introduced substance in the brain, wherein the introduced substance is able to be imaged; and
create an updated model of the area of the brain outside the pathologic lesion based on the estimates obtained from the introduced substance.

43. The system of claim 38, wherein the model of the area of the brain including the region of interest comprises a model of the area of the brain outside the pathological lesion, and wherein the computer is further configured to:
analyze radiological imaging of a brain of a particular patient; and
create a patient specific flow model utilizing the model of the area of the brain outside the pathological lesion and the radiological imaging of the brain of the particular patient.

44. The system of claim 43, wherein the computer is further configured to:
analyze radiological imaging recurrence data as a disease progresses; and
create an updated patient specific flow model utilizing the patient specific flow model and the radiological imaging recurrence data.

45. The system of claim 43, wherein the computer is further configured to:
obtain a radiation therapy plan;
determine if the radiation therapy plan covers predicted recurrence zones utilizing the patient specific flow model and the radiation therapy plan, and
if the radiation therapy plan covers significant predicted recurrence zones, proceeding with the radiation therapy plan.

46. The system of claim 45, wherein the computer is further configured to:
if the radiation therapy plan does not cover significant predicted recurrence zones, determine if any recurrence zones are in radiation resistant matter; and
if any recurrence zones are in radiation resistant matter, create an updated therapy plan which accounts for the recurrence zones in the radiation resistant matter.

47. The system of claim 46, wherein the updated therapy plan includes:
an updated radiation therapy plan;
a surgery plan; and/or
a drug delivery plan.

48. The system of claim 47, wherein the computer is further configured to:
if the recurrence zones are not in the radiation resistant matter, determine if any recurrence zones are in vital tissue; and
if any recurrence zones are in vital tissue, create an updated therapy plan which accounts for the recurrence zones in the vital tissue.

49. The system of claim 48, wherein the computer is further configured to:
if none of the recurrence zones are in vital tissue, create an updated radiation therapy plan which expands the recurrence zones and/or augments a planned dose.

50. The system of claim 49, wherein the model of the area of the brain including the region of interest comprises a model of the area of the brain outside the pathological lesion, and wherein the physiological model, an interstitial model, and the model of the area of the brain outside the pathological lesion are made under normal or diseased conditions.

51. The system of claim 50, wherein the diseased conditions comprise:
a primary brain tumor and/or Alzheimer's disease with deposition of plaque.

52. The system of claim 47, wherein the updated therapy plan includes:
an updated radiation therapy plan;
a surgery plan; and/or
a drug delivery plan.

53. The system of claim 43, wherein the model of the area of the brain including the region of interest comprises a model of the area of the brain outside the pathological lesion, and wherein computer is further configured to:
obtain a surgical resection plan;
determine if the surgical resection plan covers significant predicted recurrence zones utilizing the patient specific flow model and the surgical resection plan; and
if the surgical resection plan covers significant predicted recurrence zones, proceeding with the surgical resection plan.

54. The system of claim 53, wherein the computer is further configured to:
if the surgical resection plan does not cover significant predicted recurrence zones, determine if recurrence is widespread; and
if the recurrence is widespread, create an updated surgical resection plan based on the widespread recurrence.

55. The system of claim 54, wherein the computer is further configured to:
if the recurrence is not widespread, create an updated surgical resection plan including more aggressive surgery.

56. The system of claim 38, wherein the computer is further configured to:
obtain a cell movement model of a brain;
obtain a stem cell migration model of the brain utilizing the model of the area of the brain outside the pathological lesion and the cell movement model;
analyze radiological imaging of the brain of a particular patient; and
create a patient specific cell migration model of the patient's brain utilizing the model of the area of the brain outside the pathological lesion and the radiological imaging of the brain of the particular patient.

57. The system of claim 38, wherein the computer is further configured to:
create a trans-capillary exchange model which estimates where and how easily chemotherapy molecular material moves in and out of a brain utilizing the physiological states model; and
create a chemotherapy delivery model utilizing the trans-capillary exchange model.

58. The system of claim 57, wherein the computer is further configured to:
analyze radiological imaging of the brain of a particular patient; and
create predictions regarding functional capillary density, capillary perfusion, disruption of the blood-brain barrier and molecular permeability, and/or intracerebral pressure utilizing the model of the area of the brain outside the pathologic lesion, the chemotherapy delivery model, and the radiological imaging of the brain of the particular patient.

59. The system of claim 38, wherein the computer is further configured to:
obtain estimates of chemotherapeutic delivery based on a movement of an introduced substance in the brain; and
obtaining an updated chemotherapy delivery model based on the estimates obtained from the introduced substance.

60. The system of claim 59, wherein the computer is further configured to:
obtain a radiation therapy plan;
select perfusion imaging to quantify altered blood brain barrier permeabilities;
obtain a chemotherapy delivery model;
analyze radiological imaging of the brain of a particular patient; and
create a patient specific cell migration model of the patient's brain utilizing the radiation therapy plan, the selected perfusion imaging, the chemotherapy delivery model, and the radiological imaging of the brain of the particular patient.

61. The system of claim 38, wherein the individual is an animal and/or a human.

62. The system of claim 38, where the radiological imaging information comprises magnetic resonance imaging (MRI), including diffusion-weighted imaging (DWI), diffusion tensor imaging (DTI), dynamic contrast enhanced imaging (DCE), and/or arterial spin labeling (ASL).

63. The system of claim 62, wherein the ASL is with magnetization transfer imaging (MTI).

64. The system of claim 38, wherein the physiological states model comprises a mathematical model of transport of hydrophilic plasma proteins across the blood vessel.

65. The system of claim 38, wherein the model of the area of the brain including the region of interest comprises a model of the area of the brain outside the pathological lesion, and wherein the model of the area of the brain outside the pathological lesion accounts for:
variations in hydrophilic proteins in an interstitium of a brain of a living patient;
variations in the interstitial pressure in the brain of the living patient;
mapping migration of a primary brain tumor cells;
likely sites of recurrence of the primary brain tumor cells;
mapping extracellular fluid pathways in the brain relevant for the deposition of amyloid plaque in Alzheimer's disease; or
planning therapy to dissolve the deposited plaque; or
any combination thereof.

66. The system of claim 38, wherein the model of the area of the brain including the region of interest comprises a model of the area of the brain outside the pathological lesion, and wherein the radiological imaging is specialized to delineate Virchow-Robin spaces and the model of the area of the brain outside the pathological lesion is used to predict likely migration and deposition sites for coagulated proteins manufactured by diseased cortical neurons.

67. The system of claim 38, wherein the computer is further configured to:
- obtain drug characteristics of a drug and ex-vivo prior data for the individual;
- obtain pharmacokinetic model utilizing drug characteristics and ex-vivo prior data;
- obtain an estimate of systemic concentration of the drug utilizing a pharmacokinetic model;
- transmit the drug into a central nervous system (CNS);
- determine if an adequate dose of the drug was used for testing;
- if the dose was adequate for testing, obtain spatial patterning of kinetics of the drug in-vivo; and
- obtain efficacious drug delivery, testing, and/or monitoring protocols for CNS pharmaceuticals.

68. The system of claim 67, wherein the computer is further configured to:
- if the dose was not adequate for testing, modify the delivery plan by taking into account a pharmaceutical drug delivery plan and a chemotherapy delivery model.

69. The system of claim 38, wherein the model of the area of the brain including the region of interest comprises a model of the area of the brain outside the pathological lesion, and wherein the display comprises a user interface to display the model of the area of the brain outside the pathological lesion.

70. The system of claim 38, wherein the display comprises:
- a user interface configured to accept information utilized by the application and display information generated by the application.

71. The system of claim 38, wherein the radiological imaging is obtained from a magnetic resonance imaging apparatus capable of:
- obtain high resolution T2-weighted imaging; and/or
- control diffusion times and gradient strengths in diffusion weighted imaging.

72. The system of claim 38, wherein the sources and/or directions of interstitial flow are obtained by:
- intravenous application of manganese chloride or other contrast reagents for radiological imaging; and/or
- depositing or injecting nanoparticles in brain parenchyma.

73. The system of claim 34, wherein the computer is further configured to obtain particulate material flow and distribution in the region of interest using the physiological states model.

74. The system of claim 73, wherein the particulate material is:
- cellular material;
- molecular material; and/or
- viral material.

75. The system of claim 74, wherein the computer is further configured to:
- determine likely plaque migration pathways and/or deposition sites utilizing the patient specific flow model; and
- determine requirements for delivery of plaque dissolution agents.

76. The system of claim 38, wherein the computer is further configured to obtain pressure variations in the region of interest using the physiological states model.

* * * * *